US008898037B2

(12) United States Patent
Watson et al.

(10) Patent No.: US 8,898,037 B2
(45) Date of Patent: Nov. 25, 2014

(54) SYSTEMS AND METHODS FOR SIGNAL MONITORING USING LISSAJOUS FIGURES

(75) Inventors: James N. Watson, Dunfermline (GB); Paul Stanley Addison, Edinburgh (GB)

(73) Assignee: Nellcor Puritan Bennett Ireland, Galway (IE)

( * ) Notice: Subject to any disclaimer, the term of this patent is extended or adjusted under 35 U.S.C. 154(b) by 1060 days.

(21) Appl. No.: 12/769,413

(22) Filed: Apr. 28, 2010

(65) Prior Publication Data

US 2011/0270579 A1 Nov. 3, 2011

(51) Int. Cl.
*A61B 5/00* (2006.01)
*G06F 15/00* (2006.01)
*G06F 19/00* (2011.01)
*A61B 5/1455* (2006.01)

(52) U.S. Cl.
CPC ........... *G06F 19/3412* (2013.01); *A61B 5/7239* (2013.01); *A61B 5/7264* (2013.01); *A61B 5/742* (2013.01); *A61B 5/14551* (2013.01)
USPC ........................................... 702/189; 702/179

(58) Field of Classification Search
CPC .... A61B 5/7225; A61B 5/726; A61B 5/7275; A61B 5/7278
USPC .................................................. 702/179, 189
See application file for complete search history.

(56) References Cited

U.S. PATENT DOCUMENTS 3,835,840 A 9/1974 Mount
4,561,447 A 12/1985 Kawamura et al.
4,676,253 A 6/1987 Newman
4,729,382 A 3/1988 Schaffer
4,830,017 A 5/1989 Perry
4,836,213 A 6/1989 Wenzel et al.
4,854,327 A 8/1989 Kunig
4,898,176 A 2/1990 Petre
4,924,871 A 5/1990 Honeyager
4,928,700 A 5/1990 Harada
4,951,679 A 8/1990 Harada
4,976,268 A 12/1990 Kurosawa et al.
4,987,900 A 1/1991 Eckerle
5,065,765 A 11/1991 Eckerle
5,103,831 A 4/1992 Niwa
5,105,815 A 4/1992 Hall et al.

(Continued)

FOREIGN PATENT DOCUMENTS

EP 0443267 8/1991
EP 0755221 1/1997

(Continued)

OTHER PUBLICATIONS

Salivahanan, Electronic Devices and Circuits, Tata McGraw-Hill Education, 1998, pp. 580.*

(Continued)

*Primary Examiner* — Janet Suglo
*Assistant Examiner* — Michael Dalbo
(74) *Attorney, Agent, or Firm* — Shvarts & Leiz LLP

(57) ABSTRACT

Methods and systems are provided for generating Lissajous figures based on monitored signals and identifying features of Lissajous figures. Features may include similarity metrics, shape change metrics and noise metrics, and may be used to determine information about the monitored signal. Features may also be used in monitoring operations, such as measurement quality assessment and recalibration.

22 Claims, 12 Drawing Sheets

(56) References Cited

U.S. PATENT DOCUMENTS 5,119,824 A 6/1992 Niwa
5,131,400 A 7/1992 Harada
5,163,328 A 11/1992 Holland
5,170,796 A 12/1992 Kobayashi
5,176,143 A 1/1993 Eckerle et al.
5,178,154 A 1/1993 Ackmann et al.
5,179,956 A 1/1993 Harada et al.
5,204,922 A 4/1993 Weir
5,238,000 A 8/1993 Niwa
5,241,964 A 9/1993 McQuilkin
5,255,686 A 10/1993 Takeda et al.
5,269,312 A 12/1993 Kawamura et al.
5,289,823 A 3/1994 Eckerle
5,309,917 A 5/1994 Wang
5,431,159 A 7/1995 Baker
5,450,852 A 9/1995 Archibald et al.
5,467,771 A 11/1995 Narimatsu
5,490,506 A 2/1996 Takatani
5,494,043 A 2/1996 O'Sullivan et al.
5,497,779 A 3/1996 Takaya
5,505,209 A 4/1996 Reining
5,533,511 A 7/1996 Kaspari
5,535,753 A 7/1996 Petrucelli et al.
5,562,621 A 10/1996 Claude et al.
5,564,427 A 10/1996 Aso et al.
5,575,284 A 11/1996 Athan
5,617,868 A 4/1997 Harada
5,640,964 A 6/1997 Archibald et al.
5,649,542 A 7/1997 Archibald et al.
5,649,543 A 7/1997 Hosaka et al.
5,676,140 A 10/1997 Ukawa
5,682,898 A 11/1997 Aung
5,685,316 A 11/1997 Schookin et al.
5,704,362 A 1/1998 Hersh et al.
5,709,212 A 1/1998 Sugo
5,720,292 A 2/1998 Poliac
5,722,414 A 3/1998 Archibald et al.
5,738,103 A 4/1998 Poliac
5,743,856 A 4/1998 Oka et al.
5,755,669 A 5/1998 Ono et al.
5,762,610 A 6/1998 Narimatsu
5,772,601 A 6/1998 Oka
5,772,602 A 6/1998 Sakai
5,776,071 A 7/1998 Inukai
5,785,659 A 7/1998 Caro et al.
5,791,347 A 8/1998 Flaherty et al.
5,797,395 A 8/1998 Martin
5,797,850 A 8/1998 Archibald et al.
5,810,736 A 9/1998 Pail
5,827,181 A 10/1998 Dias
5,830,131 A 11/1998 Caro et al.
5,832,924 A 11/1998 Archibald et al.
5,833,618 A 11/1998 Caro
5,848,970 A 12/1998 Voss
5,857,975 A 1/1999 Golub
5,873,834 A 2/1999 Yanagi et al.
5,904,654 A 5/1999 Wohltmann et al.
5,941,828 A 8/1999 Archibald et al.
5,964,711 A 10/1999 Voss
6,002,952 A 12/1999 Diab
6,004,274 A 12/1999 Nolan
6,007,492 A 12/1999 Goto et al.
6,011,986 A 1/2000 Diab et al.
6,018,673 A * 1/2000 Chin et al. .................... 600/322
6,022,320 A 2/2000 Ogura
6,027,452 A 2/2000 Flaherty et al.
6,027,453 A 2/2000 Miwa
6,027,455 A 2/2000 Inukai et al.
6,045,509 A 4/2000 Caro et al.
6,067,462 A 5/2000 Diab
6,083,171 A 7/2000 Ono et al.
6,095,987 A 8/2000 Shmulewitz
6,135,966 A 10/2000 Ko
6,157,850 A 12/2000 Diab et al.
6,159,157 A 12/2000 Archibald et al.
6,161,038 A 12/2000 Schookin et al.
6,186,954 B1 2/2001 Narimatsu
6,186,955 B1 2/2001 Baura
6,190,382 B1 2/2001 Ormsby et al.
6,196,974 B1 3/2001 Miwa
6,217,524 B1 4/2001 Orr et al.
6,227,196 B1 5/2001 Jaffe et al.
6,228,034 B1 5/2001 Voss et al.
6,241,661 B1 6/2001 Schluess et al.
6,241,679 B1 6/2001 Curran
6,245,022 B1 6/2001 Archibald et al.
6,251,081 B1 6/2001 Narimatsu
6,263,222 B1 7/2001 Diab et al.
6,292,689 B1 9/2001 Wallace
6,293,915 B1 9/2001 Amano et al.
6,299,582 B1 10/2001 Brockway et al.
6,332,867 B1 12/2001 Chen et al.
6,350,242 B1 2/2002 Doten et al.
6,371,921 B1 4/2002 Caro
6,443,905 B1 9/2002 Nissila et al.
6,463,311 B1 10/2002 Diab
6,471,646 B1 10/2002 Thede
6,471,655 B1 10/2002 Baura
6,506,161 B2 1/2003 Brockway et al.
6,514,211 B1 2/2003 Baura
6,524,240 B1 2/2003 Thede
6,561,986 B2 5/2003 Baura
6,589,185 B1 7/2003 Archibald et al.
6,602,199 B2 8/2003 Chen et al.
6,602,201 B1 8/2003 Hepp et al.
6,606,511 B1 8/2003 Ali et al.
6,626,839 B2 9/2003 Doten et al.
6,631,281 B1 10/2003 Kastle
6,645,156 B2 11/2003 Oka
6,658,277 B2 12/2003 Wasserman
6,684,090 B2 1/2004 Ali et al.
RE38,476 E 3/2004 Diab et al.
6,699,194 B1 3/2004 Diab
6,767,328 B2 7/2004 Kulik
6,773,397 B2 8/2004 Kelly
6,783,498 B2 8/2004 Sackner
6,816,741 B2 11/2004 Diab
6,822,564 B2 11/2004 Al-Ali
6,826,419 B2 11/2004 Diab
6,827,688 B2 12/2004 Goto et al.
6,852,083 B2 2/2005 Caro
6,855,112 B2 2/2005 Kao
6,863,652 B2 3/2005 Huang et al.
6,869,403 B2 3/2005 Narimatsu et al.
6,929,610 B2 8/2005 Forstner
6,996,427 B2 2/2006 Ali et al.
7,004,907 B2 2/2006 Banet
7,043,293 B1 5/2006 Baura
7,044,918 B2 5/2006 Diab
7,070,566 B2 7/2006 Medero et al.
7,074,192 B2 7/2006 Friedman et al.
7,079,035 B2 7/2006 Bock et al.
7,087,025 B2 8/2006 Baruch
7,184,809 B1 2/2007 Sterling
7,215,984 B2 5/2007 Diab et al.
7,215,986 B2 5/2007 Diab et al.
7,252,636 B2 8/2007 Brown
7,320,030 B2 1/2008 Brown
7,335,162 B2 2/2008 Eide
7,376,238 B1 5/2008 Rivas et al.
7,390,300 B2 6/2008 Inukai
7,390,301 B2 6/2008 Skrabal
7,393,327 B2 7/2008 Inukai
7,400,257 B2 7/2008 Rivas
7,455,643 B1 11/2008 Li et al.
7,481,772 B2 1/2009 Banet
7,485,095 B2 2/2009 Shusterman
2005/0148885 A1 7/2005 Tweed et al.
2005/0177046 A1* 8/2005 Mills ............................ 600/481
2005/0197579 A1* 9/2005 Baker, Jr. ...................... 600/473
2005/0251344 A1 11/2005 Appel et al.
2005/0261594 A1 11/2005 Banet
2006/0009700 A1 1/2006 Brumfield et al.
2006/0063992 A1 3/2006 Yu et al.

(56) References Cited

U.S. PATENT DOCUMENTS

| | | | | |
|---|---|---|---|---|
| 2006/0063993 | A1 | 3/2006 | Yu et al. | |
| 2006/0079945 | A1 | 4/2006 | Libbus | |
| 2006/0200015 | A1* | 9/2006 | Baker, Jr. | 600/323 |
| 2006/0206021 | A1 | 9/2006 | Diab | |
| 2006/0217614 | A1 | 9/2006 | Takala et al. | |
| 2006/0217628 | A1 | 9/2006 | Huiku | |
| 2006/0241975 | A1 | 10/2006 | Brown | |
| 2006/0258921 | A1* | 11/2006 | Addison et al. | 600/323 |
| 2006/0281983 | A1* | 12/2006 | Al-Ali et al. | 600/323 |
| 2006/0285736 | A1 | 12/2006 | Brown | |
| 2006/0287603 | A1 | 12/2006 | Bartnik et al. | |
| 2007/0066910 | A1 | 3/2007 | Inukai et al. | |
| 2007/0083093 | A1 | 4/2007 | Diab | |
| 2007/0118045 | A1 | 5/2007 | Naghavi et al. | |
| 2007/0225582 | A1 | 9/2007 | Diab et al. | |
| 2007/0249467 | A1 | 10/2007 | Hong et al. | |
| 2007/0276262 | A1* | 11/2007 | Banet et al. | 600/485 |
| 2007/0276632 | A1* | 11/2007 | Banet et al. | 702/187 |
| 2008/0015451 | A1 | 1/2008 | Hatib et al. | |
| 2008/0030468 | A1 | 2/2008 | Ali et al. | |
| 2008/0033305 | A1 | 2/2008 | Hatib et al. | |
| 2008/0077022 | A1* | 3/2008 | Baker | 600/500 |
| 2008/0132798 | A1 | 6/2008 | Hong et al. | |
| 2008/0214903 | A1 | 9/2008 | Orbach | |
| 2008/0214942 | A1 | 9/2008 | Oh et al. | |
| 2008/0242955 | A1 | 10/2008 | Uutela et al. | |
| 2008/0255436 | A1* | 10/2008 | Baker | 600/323 |
| 2009/0048497 | A1 | 2/2009 | Keren | |
| 2009/0076398 | A1* | 3/2009 | Li et al. | 600/494 |

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 03-225268 | 12/2003 |

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. S11-S14.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994, pp. 1-446.

Fung, YC, Biomechanics: Circulation, 2nd Edition, New York, Springer, 1997, pp. 1-571.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, Feb. 1991, pp. 39-54.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

* cited by examiner

SYSTEMS AND METHODS FOR SIGNAL MONITORING USING LISSAJOUS FIGURES

SUMMARY

The present disclosure relates to signal analysis and, more particularly, the present disclosure relates to using Lissajous figures in signal analysis and monitoring.

Electronic patient monitors play a critical role in medical diagnosis and treatment, both inside and outside the clinical setting. In particular, monitors that analyze a patient's physiological signals can often perform analyses that uncover changes in patient condition that are difficult for a human clinician to detect from displayed signals alone. Many such monitors utilize one or more signal processing steps to determine useful information from a measured signal.

In general, a Lissajous figure may represent two or more two signals whose relationship communicates information regarding an underlying process, such as a physiological process. The comparison may take the form of a plot in two or more dimensions of a trajectory of the two or more signals, wherein each signal may be represented by an axis. A signal represented by a Lissajous figure may be a received signal, a transformation of a received signal, a mathematical manipulation of a received signal, or any combination thereof. Useful information about the underlying process may be determined by analyzing one or more Lissajous figures.

For example, a patient's blood oxygen saturation, among other physiological information, may be determined at least in part by analyzing a Lissajous figure of photoplethysmograph (PPG) signals obtained from the patient. In some applications, a Lissajous figure may be used to represent a PPG signal at a Red electromagnetic frequency and a PPG signal at an Infrared (IR) electromagnetic frequency, with both PPG signals measured at a single site on a patient's body. It is known that these two PPG signals may be related by a fixed ratio which is dependent upon the blood oxygen saturation of the patient, and thus may be expected to lie on a straight line when plotted against one another. In the presence of noise or changes in monitoring conditions, however, corresponding points in such a Lissajous figure representing Red and IR PPG signals may not lie on a straight line. Instead, the Lissajous figure may include more irregular trajectories. Irregular trajectories may be caused, for example, by a noise source that differentially affects the Red and IR PPG signals. Accordingly, examining a Lissajous figure that exhibits irregular trajectories may reveal characteristics of a noise source affecting one or more of the represented signals.

Additional information about patient condition and monitoring status may be communicated by Lissajous figures representing different types of signals. For example, a Lissajous figure may represent a PPG signal taken at a first body site (e.g., an IR PPG signal measured at a patient's ear) and a PPG signal taken at a second, different body site (e.g., an IR PPG signal measured at a patient's finger). The form of such a Lissajous figure depends on the morphology of the two signals represented. If the morphologies are identical and in phase, the resulting points in the Lissajous figure may appear to approximately fall along a straight line. In general, however, the morphology of the signals obtained at two different sites may be quite different due to differential propagation environments of pulse waves near the different sites, and may be out-of-phase due to differing distances of the two sites from the heart. Additionally, noise affecting one or more of the signals represented in a Lissajous figure may influence the figure's form.

Features of a Lissajous figure may be used to identify short- or long-term changes in the morphology of the signals. For example, a feature of a first Lissajous figure may be compared to a feature of a Lissajous figure measured at a calibration point, or to a feature of an archetypal Lissajous figure. A transient, or short-term, change in a feature of a Lissajous figure may indicate a region of noise in the signal, and may indicate that any measurement based on such a region should be treated accordingly in a monitoring operation (e.g., given a lower weighting in a weighted average). A longer-term change in a feature of a Lissajous figure may indicate a change in signal morphology, which in turn may indicate a change in a patient's physiological state.

Identifying one or more features of Lissajous figures, or a change in one or more features of Lissajous figures, may allow different physiological conditions to be distinguished by a patient monitoring system. For example, a continuous non-invasive blood pressure (CNIBP) monitoring system may determine a blood pressure or other physiological parameter based at least in part on a differential pulse transit time (DPTT), which be measured between multiple sensors located at multiple body sites. Changes in DPTT may arise from a change in a patient's blood pressure, or may arise from other physiological changes, such as a change in patient posture or a change in blood vessel compliance. These differing sources of a change in DPTT may be distinguished by monitoring one or more features of a Lissajous figure representing the signals measured at the multiple body sites. Examples of such features include the distribution of point to point gradients in the figure and the principal components of the points of the figure. Additionally, the presence or position of additional loops in the figure may be associated with dichrotic notch-like features in one or more PPG signals (e.g., as used in a DPTT determination). These features may indicate changes in dispersion characteristics of the pulse wave and changes in peripheral resistance which, in turn, may be associated with changes in blood pressure, changes in vasotone, changes in disease state (e.g., vessel occlusions), and/or other physiological conditions.

Features of a Lissajous figure may communicate information about measurement quality and/or indicate a need for recalibration of a monitoring system. For example, changes in a feature of a Lissajous figure may suggest the introduction of a new noise source into the monitoring environment causing decreased measurement quality. A change in a feature of a Lissajous figure may suggest that recalibration be delayed until an improvement in measurement quality is detected. A feature of a Lissajous figure may also correspond to a change in patient condition (e.g., when a patient is given a drug which alters his or her physiological state). Such a change in patient condition may require a recalibration of the monitoring device, or may suggest that the calculation of physiological parameters based on the monitored signals be delayed or adjusted. Accordingly, there is a need for monitoring devices that employ computationally-efficient metrics for determining features of Lissajous figures and that use this information in monitoring operations. The methods and systems described herein address these needs by identifying features of Lissajous figures based on monitored signals and using these features to determine information about the monitoring process.

The methods and systems of the present disclosure will be illustrated with reference to the monitoring of a physiological signal (which may be a PPG signal); however, it will be understood that the disclosure is not limited to monitoring physiological signals and is usefully applied within a number of signal monitoring settings. Those skilled in the art will recognize that the present disclosure has wide applicability to other signals including, but not limited to, other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

BRIEF DESCRIPTION OF THE DRAWINGS

The above and other features of the present disclosure, its nature and various advantages will be more apparent upon consideration of the following detailed description, taken in conjunction with the accompanying drawings in which:

FIG. 2(*b*) is a block diagram of an illustrative patient monitoring system coupled to a patient in accordance with an embodiment;

FIG. 3(*c*) shows an illustrative scalogram derived from a signal containing two pertinent components in accordance with an embodiment;

FIG. 3(*d*) shows an illustrative schematic of signals associated with a ridge in the scalogram of FIG. 3(*c*), and illustrative schematics of a further wavelet decomposition of these signals in accordance with an embodiment;

FIGS. 3(*e*) and 3(*f*) are flow diagrams of illustrative steps involved in performing an inverse continuous wavelet transform in accordance with an embodiment;

DETAILED DESCRIPTION

Figure 1A:
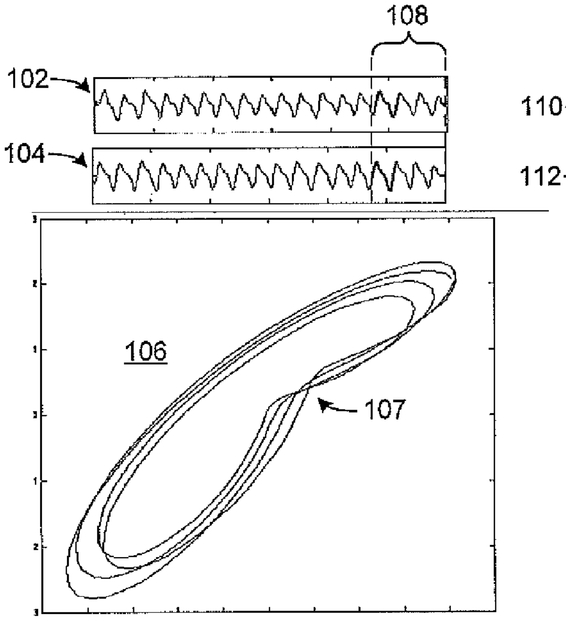
FIGS. 1(*a*)-1(*d*) depict illustrative time waveforms and corresponding Lissajous figures in accordance with an embodiment.
Figure 1B:
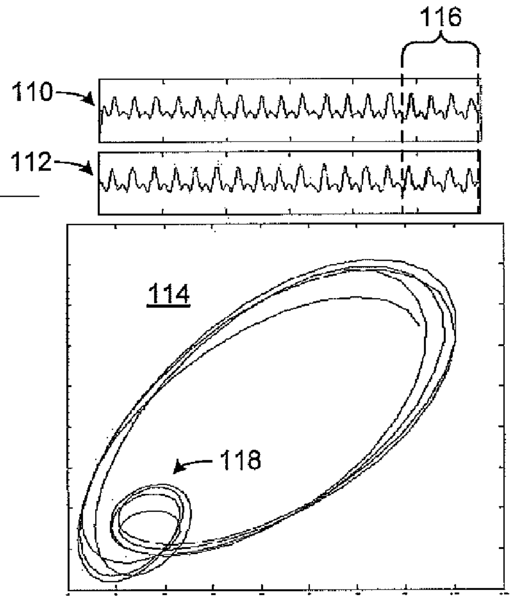
Figure 1C:
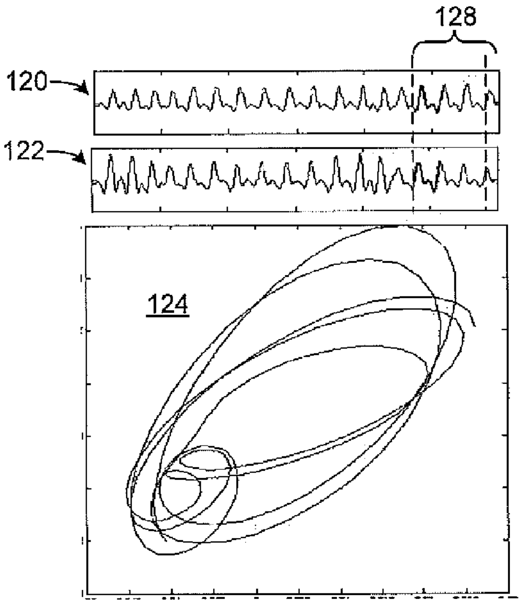
Figure 1D:
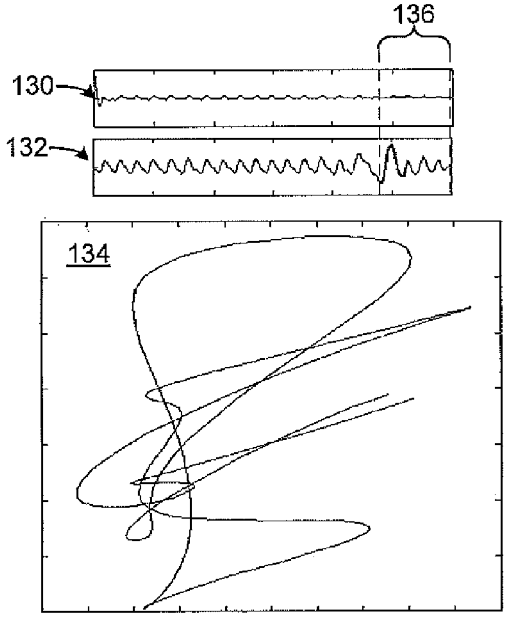

As described above, information about patient condition and monitoring status may be communicated by Lissajous figures representing different types of signals. FIGS. 1(*a*)-1(*d*) depict several illustrative examples of Lissajous figures that may be generated and analyzed using the techniques provided herein.

One illustrative construction of a Lissajous figure is depicted in FIG. 1(*a*), in which waveform 102 is a photoplethysmograph (PPG) signal taken at a patient's finger and waveform 104 is a PPG signal taken at a patient's forehead over the same interval. Lissajous figure 106 compares waveform 104 against waveform 102 over the four-second window indicated by time interval 108. Lissajous figure 106 may represent multiple cycles of a periodic process, which may be compared to each other or to an archetypal Lissajous figure of a cycle of the process. For example, Lissajous figure 106 may represent approximately four cycles of PPG waveforms that are periodic with periods of approximately 1 second (which may correspond to a patient pulse rate of approximately 60 beats per minute). In an embodiment, a Lissajous figure based on one or more physiological signals such as Lissajous figure 106 may be used to determine the frequency of periodic physiological phenomena. For example, a patient's pulse rate may be determined by analyzing Lissajous figure 106 to determine the number of cycles within the Lissajous figure over the given window of time; the ratio of the number of cycles to the length of the window may represent the patient's pulse rate. Lissajous figure 106 may exhibit one or more kinks such as kink 107. A kink may provide information on the occurrence of characteristic points in one or more of the signals represented by the Lissajous figure, including minimum points, maximum points, inflection points, or other characteristic points. In an embodiment, a kink may indicate the relative positions and degrees of inflection points in the downstroke of a pulse-based waveform. As such, a kink may indicate a level of peripheral resistance and/or (acoustic) reflection coefficients at bifurcations in an arterial tree. Changes in the position of a kink may in turn be used for measuring or monitoring blood pressure, autonomic response and vessel wall stiffness, among other patient characteristics.

In an embodiment, one or more of the signals represented in a Lissajous figure may be a time derivative signal. Taking a time derivative of a signal may result in increased similarity between the two or more signals represented in a Lissajous figure and may allow additional information to be obtained when analyzing the Lissajous figure. For example, a PPG signal may be characterized by periodic pulses, each of which may exhibit a sharp initial upstroke followed by a more gradual downstroke. This sharp initial upstroke may arise from the front of a pulsatile cardiac wave, while the more gradual downstroke may arise from the remainder of the pulsatile wave and internal reflections. While the shape of the sharp initial upstroke may be similar for PPG signals taken at any two body sites (e.g., a forehead and a toe), the more gradual downstroke may vary in shape from site to site. Taking a derivative of a PPG signal may accentuate the sharp (i.e., high gradient) initial upstroke while "flattening" or "suppressing" the more gradual (i.e., low gradient) downstroke. The time derivative of PPG signals taken from two body sites, then, may appear more similar than the non-time derivative signals.

An example of a Lissajous figure in which one or more of the represented signals is a time derivative is given by Lissajous figure 114 in FIG. 1(*b*), in which waveform 110 is a time derivative of a PPG signal taken at a patient's finger, while waveform 112 is a time derivative of a PPG signal taken at a patient's forehead over the same time interval. Lissajous figure 114 compares waveform 112 against waveform 110 over the four-second window indicated by time interval 116. As described above with reference to Lissajous figure 106 of FIG. 1(*a*), Lissajous figure 114 may be used to determine the frequency of periodic phenomena, for example, by examining the number of cycles in Lissajous figure 114. Lissajous figure 114 may also exhibit one or more loops such as loop 118. A loop may provide information on the occurrence of characteristic points in one or more of the signals represented by the Lissajous figure, including minimum points, maximum points, inflection points, or other characteristic points. In an embodiment, a loop within a Lissajous figure representing one or more PPG signals may be indicative of a dichrotic notch in one or more of the PPG signals, which may communicate information regarding a patient's peripheral resistance to blood flow. A loop may indicate an actual turning point in the downstroke of the signal. The size of the loop may therefore be indicative of the size of a notch in the signal. In an embodiment, the size of a loop relative to a main pulse loop may be used to derive a PPG augmentation index (e.g., a ratio of pulse amplitude to notch amplitude).

In FIG. 1(*c*), waveforms 120 and 122 are time derivatives of PPG signals taken at a patient's finger and forehead, respectively, but have been subject to additional noise in comparison with waveforms 110 and 112 of FIG. 1(*b*). Lissajous figure 124 compares waveform 122 against waveform 120 over the four-second window indicated by time interval 128. Compared to Lissajous figure 114, Lissajous figure 124 exhibits additional irregularity around a periodic form, indicating the presence of noise. A still higher level of noise is represented by waveforms 130 and 132 of FIG. 1(*d*), which are again time derivatives of PPG signals taken at a patient's finger and forehead, respectively. Lissajous figure 134 compares waveform 132 against waveform 130 over the four-second window indicated by time interval 136. A regular, periodic form may be difficult to identify within Lissajous figure 134. This difficulty may indicate that any measurement based on one or more of Lissajous figure 134 and waveforms 130 and 132 (e.g., a physiological measurement) may be unreliable.

The noise affecting a physiological measurement signal (e.g., a PPG signal) may arise from different sources and exhibit different characteristics. For example, patient movement may cause changes in venous blood under an optical sensor site, resulting in changes in light absorbance and thus changes in a measured optical signal. Another source of noise is sensor movement, which may cause changes in the blood volume under an optical sensor site and thus changes in a measured optical signal. It may be the case that noise from either of these sources may contain frequency components similar to the components found in the measured physiological signal (e.g., a PPG signal), which may increase the difficulty of accurately measuring the physiological phenomena of interest. The systems and techniques described herein may be used to identify noise and thus improve the quality of patient monitoring and the determination of clinical parameters. Embodiments in which features of Lissajous figures may be used to estimate signal similarity, shape changes, and/or noise are described in detail herein.

Although FIG. 1(*a*) depicts a Lissajous figure that compares a non-time derivative signal to a non-time derivative signal and FIGS. 1(*b*)-1(*d*) depict Lissajous figures that compare time derivative signals to time derivative signals, Lissajous figures may be used to represent other combinations of signals, transformed signals, and manipulated signals (such as time derivative signals). In an embodiment, a Lissajous figure may compare a time derivative signal to a non-time derivative signal. Such an embodiment may be suitable when, for example, a first monitored signal is a damped version of a second monitored signal (e.g., a first signal is a PPG signal taken at a patient's forehead, while a second signal is a PPG signal taken at a patient's finger). In this case, the time derivative of the first signal may exhibit increased similarity with the second signal than is present between the first and second signals. In an embodiment, a Lissajous figure may compare more than two signals, which may each be any one of a received signal, a transformed signal, a manipulated signal, and a combination thereof. Such a Lissajous figure may be represented in three or more dimensions. For example, a three-dimensional Lissajous figure may be based on a continuous wavelet transformations of two signals, as discussed in additional detail below.

For illustrative purposes, the systems and techniques disclosed herein may be described in the context of continuous, non-invasive blood pressure monitoring (CNIBP) systems, oximetry systems, and other patient monitoring systems. It will be understood that the disclosed systems and techniques may be suitable for any signal processing and monitoring application in which one or more signals are monitored to assess noise, identify changes in a monitored process, and/or determine information.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of light in the tissue. For example, the oximeter may measure the intensity of light that is received at a light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The time derivative of the PPG signal may also be of interest, and the term "PPG time derivative signal" will be used herein. In an embodiment, the PPG signal and/or the PPG time derivative signal may be used to calculate the amount of a blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and Infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:

$\lambda$=wavelength;

t=time;

I=intensity of light detected;

$I_0$=intensity of light transmitted;

s=oxygen saturation;

$\beta_0, \beta_r$=empirically derived absorption coefficients; and l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_0 - (s\beta_0 + (1-s)\beta_r)l. \tag{2}$$

2. Eq. 2 is then differentiated with respect to time to yield $$\frac{d\log I}{dt} = -(s\beta_o + (1-s)\beta_r)\frac{dl}{dt}. \tag{3}$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_o(\lambda_{IR}) + (1-s)\beta_r(\lambda_R)}{s\beta_o(\lambda_{IR}) + (1-s)\beta_r(\lambda_{IR})}. \tag{4}$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}. \tag{5}$$

5. Note that, in discrete time, the following approximation can be made:

$$\frac{d\log I(\lambda, t)}{dt} \simeq \log I(\lambda, t_2) - \log I(\lambda, t_1). \tag{6}$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \tag{7}$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \tag{8}$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \tag{9}$$

9. From Eq. 8, R can be calculated using two points (e.g., a PPG maximum and a PPG minimum), or a family of points. One method applies a family of points to a modified version of Eq. 8. Using the relationship $$\frac{d\log I}{dt} = \frac{dI/dt}{I}, \tag{10}$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} = \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)} = R, \tag{11}$$

which defines a cluster of points whose slope of y versus x will give R when $$x = [I(t_2, \lambda_{IR}) - I(t_1, \lambda_{IR})]I(t_1, \lambda_R), \tag{12}$$

and $$y = [I(t_2, \lambda_R) - I(t_1, \lambda_R)]I(t_1, \lambda_{IR}), \tag{13}$$

Figure 2A:
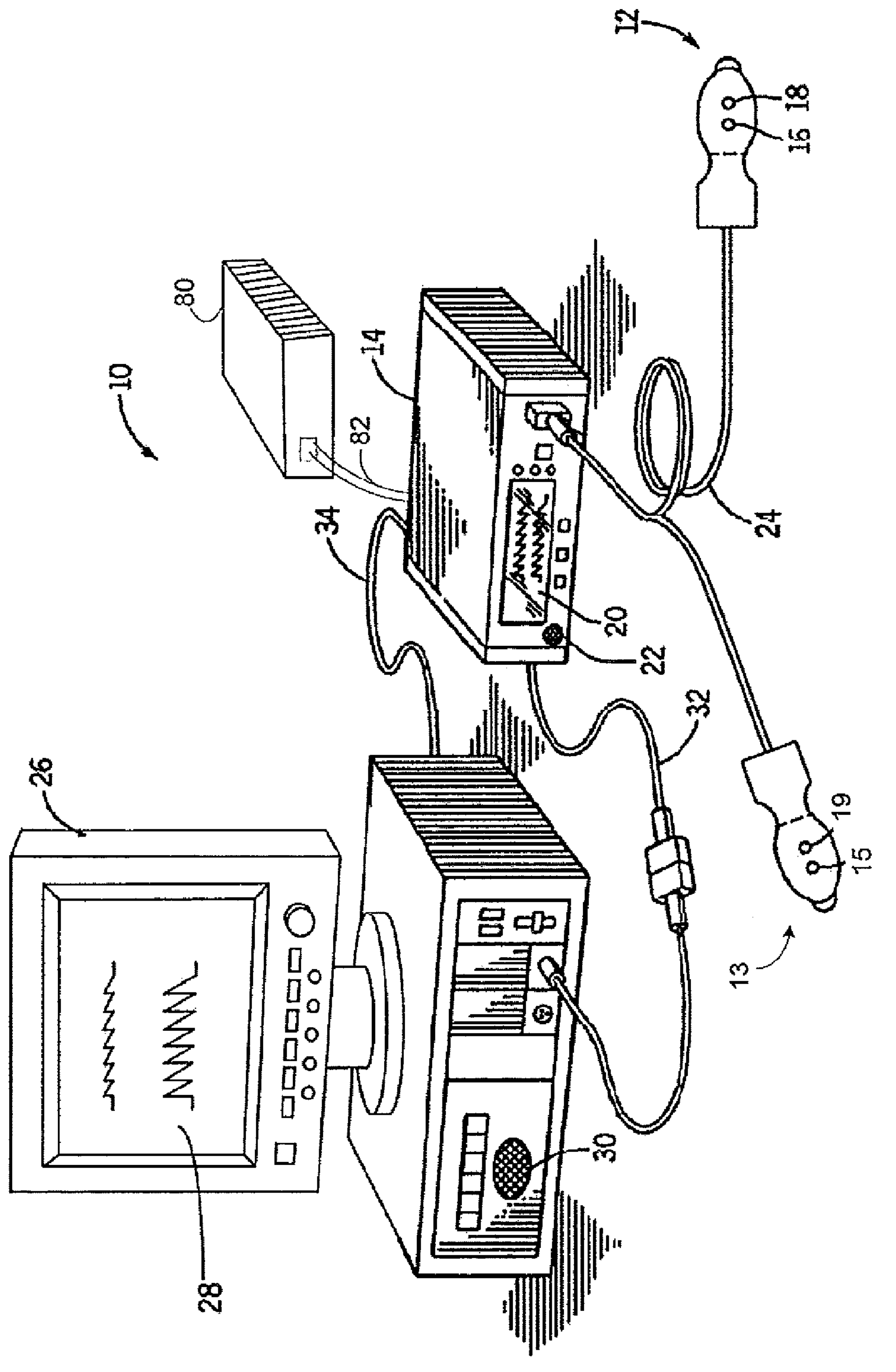
FIG. 2(*a*) shows an illustrative patient monitoring system in accordance with an embodiment.
Figure 2B:
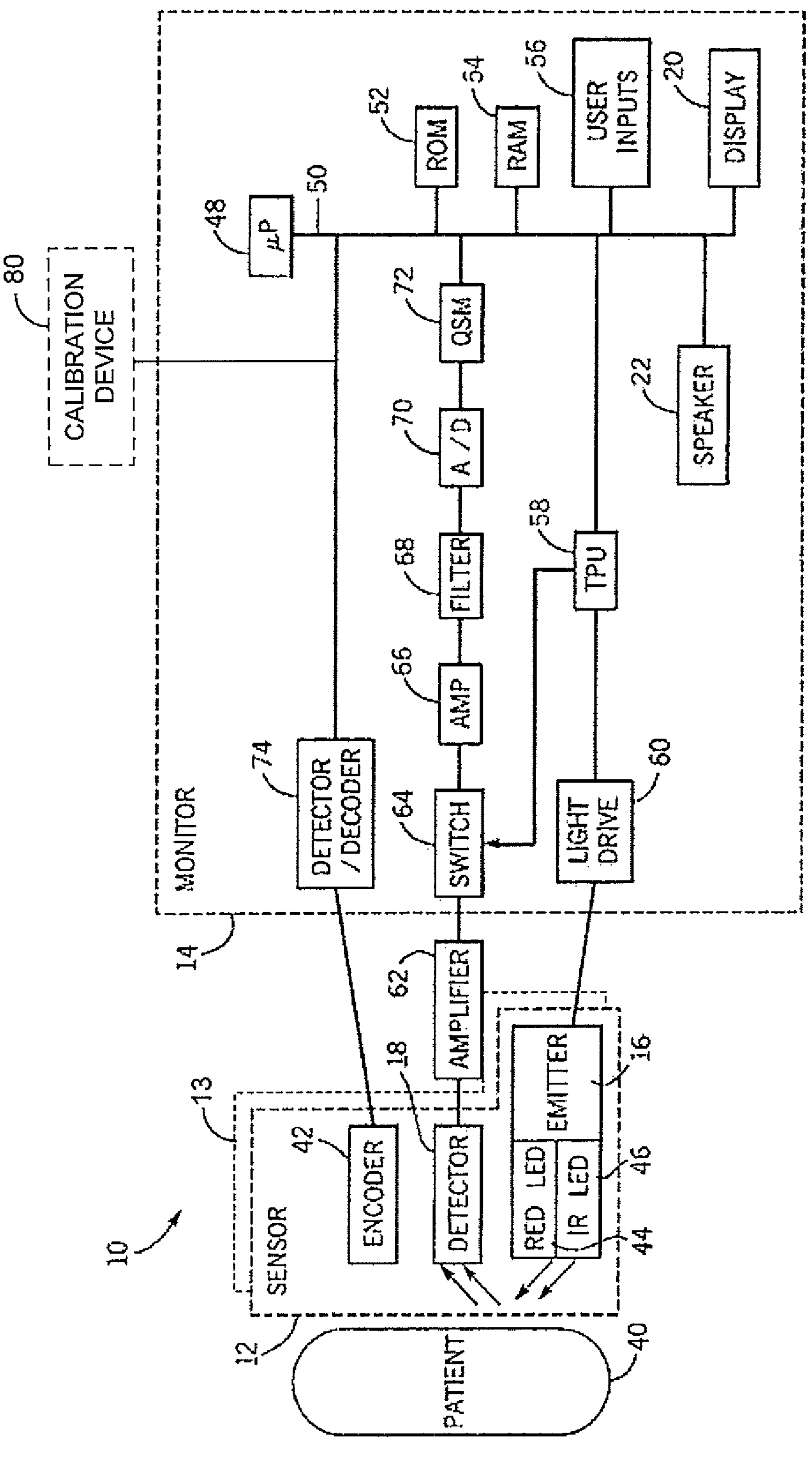
Figure 3A:
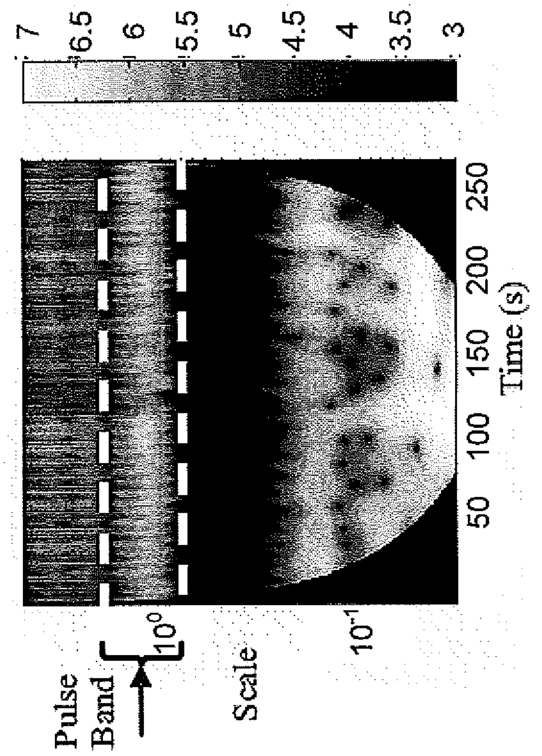
FIGS. 3(*a*) and 3(*b*) show illustrative views of a scalogram derived from a PPG signal in accordance with an embodiment.
Figure 3B:
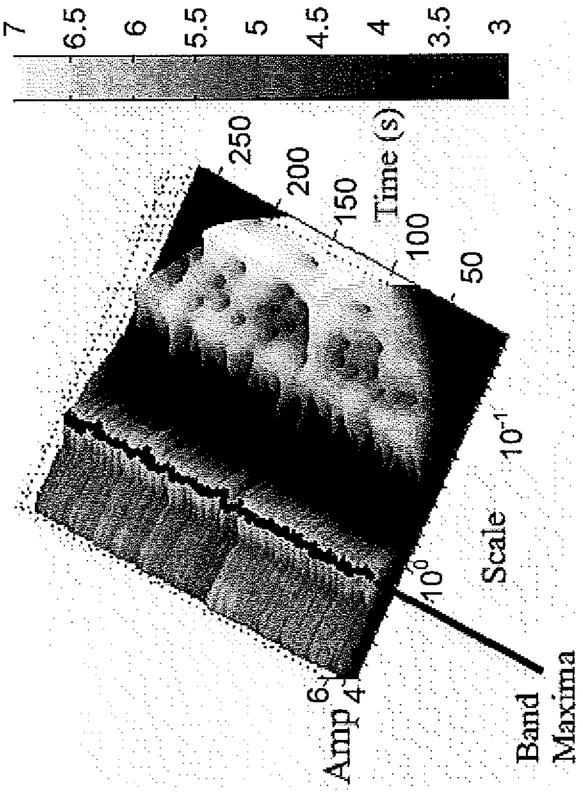
Figure 3C:
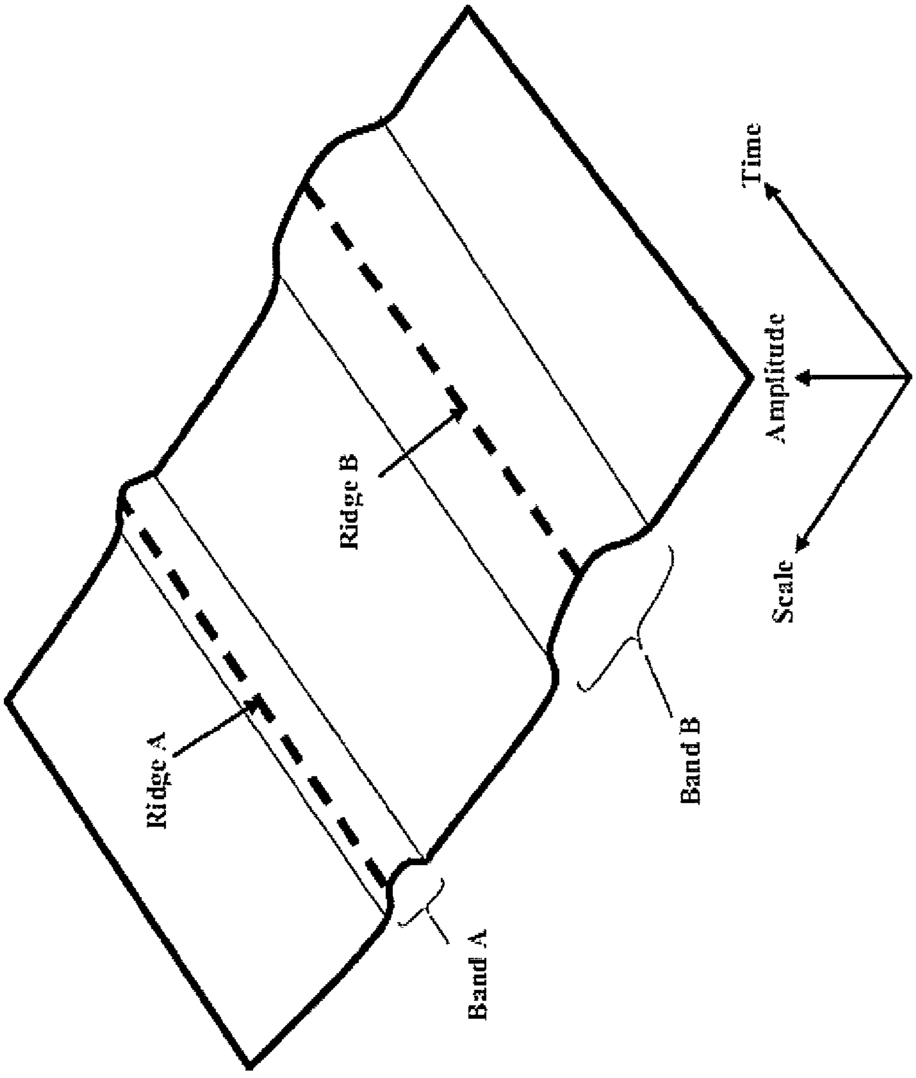
Figure 3D:
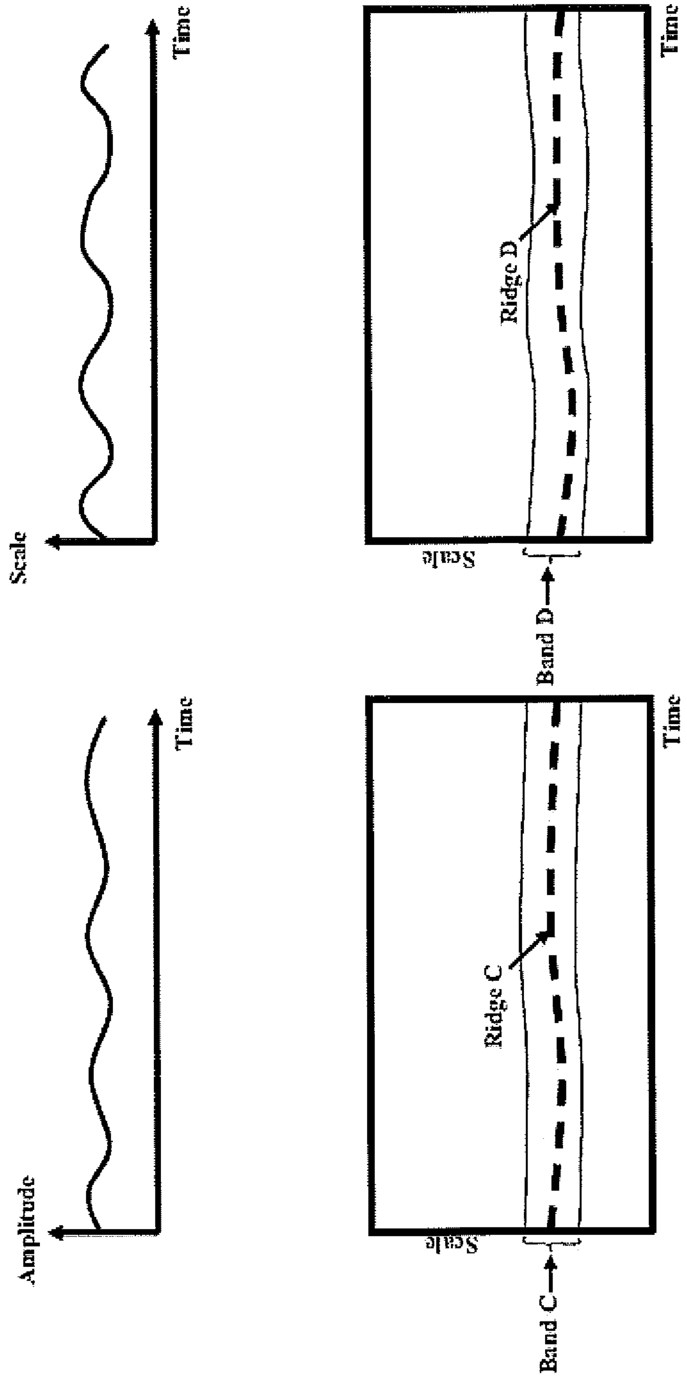
Figure 3E:
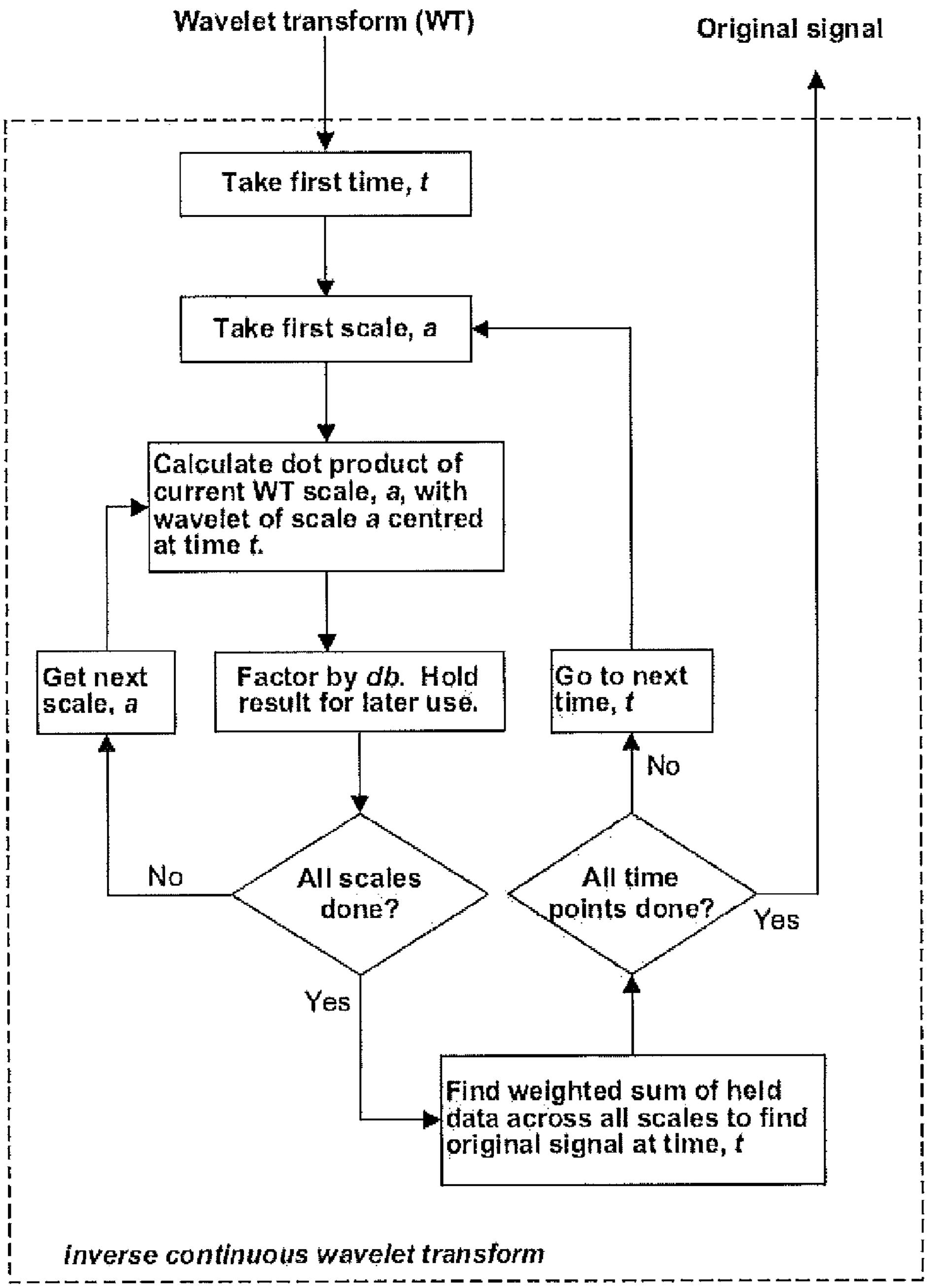
Figure 3F:
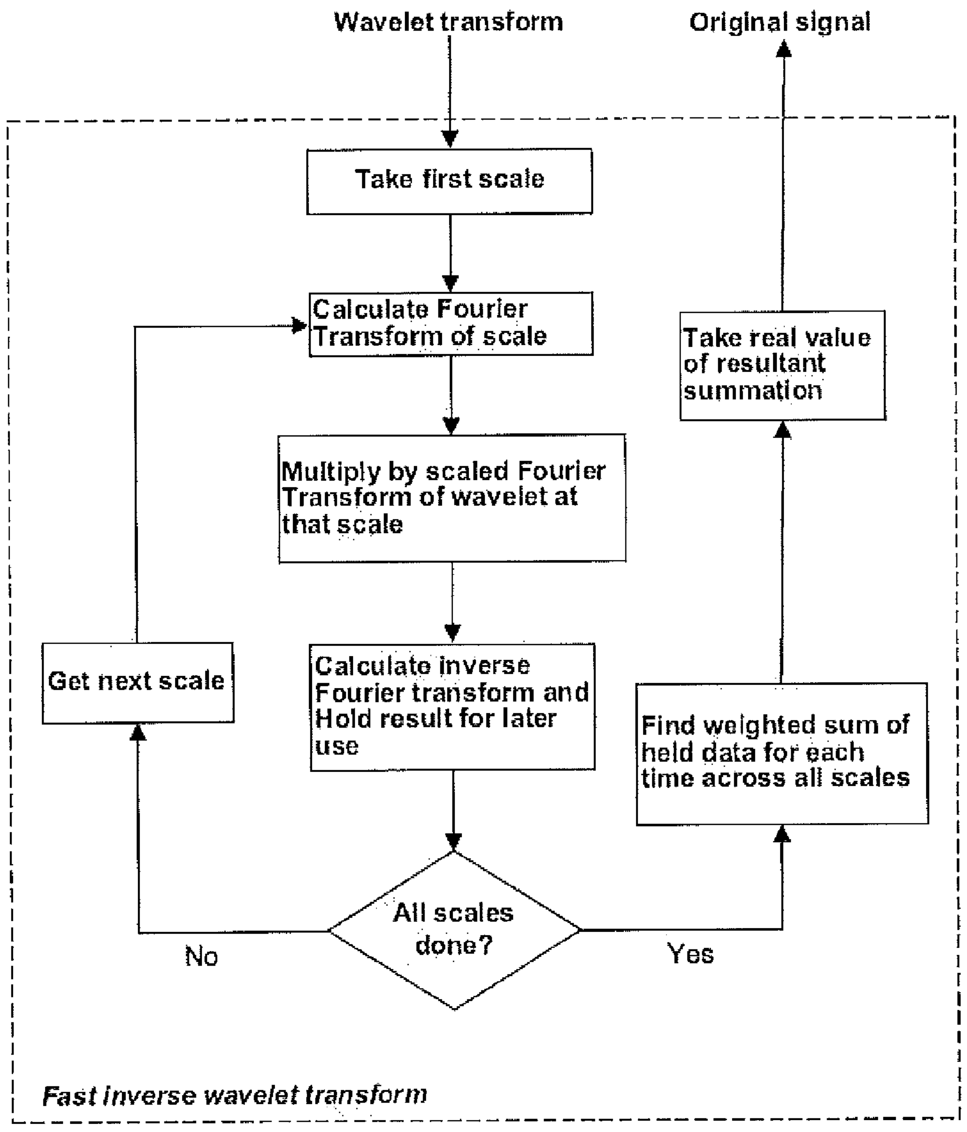

FIG. 2(*a*) shows an illustrative patient monitoring system 10. System 10 may include sensor unit 12 and monitor 14. In an embodiment, sensor unit 12 is part of a continuous, non-invasive blood pressure (CNIBP) monitoring system. In an embodiment, sensor unit 12 may include an emitter 16 for emitting light at one or more wavelengths into a patient's tissue. A detector 18 may also be provided in sensor 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. In an embodiment, system 10 may include one or more additional sensor units, such as sensor unit 13, which may take the form of any of the embodiments described herein with reference to sensor unit 12. For example, sensor unit 13 may include emitter 15 and detector 19. Sensor unit 13 may be the same type of sensor unit as sensor unit 12, or sensor unit 13 may be of a different sensor unit type than sensor unit 12. Sensor units 12 and 13 may be capable of being positioned at two different locations on a subject's body; for example, sensor unit 12 may be positioned on a patient's forehead, while sensor unit 13 may be positioned at a patient's fingertip. As discussed in additional detail below, one or more signals from one or more sensors and/or sensor units may be used in the measurement assessment techniques described herein.

Sensor units 12 and 13 may each detect one or more signals that carry information about a patient's physiological state, such as an electrocardiograph signal, an arterial line measurements and a pulsatile force exerted on the walls of an artery using, for example, oscillometric methods with a piezoelectric transducer. It will be understood that any type of sensor, including any type of physiological sensor, may be used in one or more of sensor units 12 and 13 in accordance with the systems and techniques disclosed herein. It is understood that any number of sensors measuring any number of physiological signals may be used to assess patient status in accordance with the techniques described herein.

According to an embodiment, system 10 may include a plurality of sensors forming a sensor array in lieu of either or both of sensor units 12 and 13. Each of the sensors of the sensor array may be a complementary metal oxide semiconductor (CMOS) sensor. Alternatively, each sensor of the array may be a charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

In some embodiments, the signal obtained from a sensor or probe, such as sensor unit 12, may take the form of a PPG signal obtained, for example, from a CNIBP monitoring system or pulse oximeter. In this embodiment, sensor unit 12 may include a light sensor that is placed at a site on a patient, typically a fingertip, toe, forehead or earlobe, or in the case of a neonate, across a foot. As described above, the system may use a light source to pass light through blood perfused tissue and may also photoelectrically sense the absorption of light in the tissue. For example, the system may measure the intensity of light that is received at a light sensor as a function of time. The light intensity or the amount of light absorbed may then be used to calculate physiological measurements (e.g., blood pressure and blood oxygen saturation). Techniques for obtaining blood pressure measurements from data are described in more detail in co-pending, commonly assigned U.S. patent application Ser. No. 12/242,867, filed Sep. 30, 2008, entitled "SYSTEMS AND METHODS FOR NON-INVASIVE CONTINUOUS BLOOD PRESSURE DETERMINATION" and co-pending, commonly assigned U.S. patent application Ser. No. 12/242,238, filed Sep. 30, 2008, entitled "SYSTEMS AND METHODS FOR NON-INVASIVE BLOOD PRESSURE MONITORING," which are both hereby incorporated by reference herein in their entireties.

It will be understood that the present disclosure is applicable to any suitable signals that communicate information about an underlying physiological process. It will be understood that the signals may be digital or analog. Moreover, it will be understood that the present disclosure has wide applicability to signals including, but not limited to other biosignals (e.g., electrocardiogram, electroencephalogram, electrogastrogram, phonocardiogram, electromyogram, pathological sounds, ultrasound, or any other suitable biosignal), or any combination thereof. For example, the techniques of the present disclosure could be applied to monitoring pathological sounds or arterial (or venous) pressure fluctuations.

In an embodiment, sensor unit 12 may be connected to and draw its power from monitor 14 as shown. In another embodiment, sensor unit 12 may be wirelessly connected to monitor 14 and include its own battery or similar power supply (not shown). In an embodiment, sensor unit 12 may be communicatively coupled to monitor 14 via a cable 24. However, in other embodiments, a wireless transmission device (not shown) or the like may be used instead of or in addition to cable 24.

Monitor 14 may be configured to calculate physiological parameters (e.g., heart rate, blood pressure, blood oxygen saturation) based at least in part on data received from one or more sensor units such as sensor units 12 and 13. In an alternative embodiment, the calculations may be performed on the monitoring device itself and the result of the calculations may be passed to monitor 14. Further, monitor 14 may include a display 20 configured to display the physiological parameters of a patient or information about the system. In the embodiment shown, monitor 14 may also include a speaker 22 to provide an audible sound that may be used in various other embodiments to be discussed further below, such as sounding an audible alarm in the event that a patient's physiological parameters are not within a predefined normal range. Monitor 14 may also include a measurement quality indicator, such as a graphic or text in display 20 or a tone or message via speaker 22.

In the illustrated embodiment, system 10 may also include a multi-parameter patient monitor 26. The monitor 26 may include a cathode ray tube display, a flat panel display (as shown) such as a liquid crystal display (LCD) or a plasma display, or may be any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patients blood pressure from monitor 14, blood oxygen saturation generated by monitor 14 (referred to as an "$SpO_2$" measurement), and pulse rate information from monitor 14. Monitor 26 may include a speaker 30.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14 via a cable 82, a battery, or by a conventional power source such as a wall outlet, may include any suitable physiological signal calibration device. Calibration device 80 may be communicatively coupled to monitor 14 via cable 82, and/or may communicate wirelessly (not shown). For example, calibration device 80 may take the form of any invasive or non-invasive physiological monitoring or measuring system used to generate reference physiological measurements for use in calibrating a monitoring device. For example, calibration device 80 may take the form of a blood pressure monitoring system, and may include, for example, an aneroid or mercury sphygmomanometer and occluding cuff, a tonometric device, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference physiological measurements obtained from some other source (e.g., an external invasive or non-invasive physiological measurement system).

Calibration device 80 may also access reference measurements stored in memory (e.g., RAM, ROM, or a storage device). As described in more detail below, the reference measurements generated or accessed by calibration device 80 may be updated in real-time, resulting in a continuous source of reference measurements for use in continuous or periodic calibration. Alternatively, reference measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14. Reference measurements may then be wirelessly transmitted to monitor 14 for use in calibration. In still other embodiments, calibration device 80 is completely integrated within monitor 14. For example, in some embodiments, calibration device 80 may access reference measurements from a relational database stored within calibration device 80, monitor 14, or multiparameter patient monitor 26. As described in additional detail below, calibration device 80 may be responsive to a recalibration signal, which may initiate the calibration of monitor 14 or may communicate recalibration information to calibration device 80 (e.g., according to a recalibration schedule). Calibration may be performed at any suitable time (e.g., once initially after monitoring begins) or on any suitable schedule (e.g., a periodic or event-driven schedule). In an embodiment, calibration may be initiated or delayed based at least in part on a measurement quality assessment or a recalibration initiation assessment. Techniques for recalibrating a continuous, non-invasive blood pressure (CNIBP) system are described in more detail in co-pending, commonly assigned U.S. patent application Ser. No. 12/242,858, filed Sep. 30, 2008, entitled "SYSTEMS AND METHODS FOR RECALIBRATING A NON-INVASIVE BLOOD PRESSURE MONITOR," which is hereby incorporated by reference herein in its entirety.

FIG. 2(*b*) is a block diagram of patient monitoring system 10 of FIG. 2(*a*), which may be coupled to a patient 40 in accordance with an embodiment. Certain illustrative components of sensor unit 12 and monitor 14 are illustrated in FIG. 2(*b*). Because sensor units 12 and 13 may include similar components and functionality, only sensor unit 12 will be discussed in detail for ease of illustration. It will be understood that any of the concepts, components, and operation discussed in connection with sensor unit 12 may be applied to sensor unit 13 as well (e.g., emitter 16 and detector 18 of sensor unit 12 may be similar to emitter 15 and detector 19 of sensor unit 13). It will be noted that patient monitoring system 10 may include one or more additional sensor units or probes, which may take the form of any of the embodiments described herein with reference to sensor units 12 and 13 (FIG. 2(*a*)). These additional sensor units included in system 10 may take the same form as sensor unit 12, or may take a different form. In an embodiment, multiple sensors (distributed in one or more sensor units) may be located at multiple different body sites on a patient.

Sensor unit 12 may include encoder 42. In an embodiment, encoder 42 may contain information about sensor unit 12, such as what type of sensors it includes (e.g., whether the sensor is a pressure transducer or a pulse oximeter). This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which, for example, blood pressure and other measurements may be determined based at least in part on the signal or signals received at sensor unit 12. For example, some pulse oximetry sensors rely on equations that relate an area under a pulse of a photoplethysmograph (PPG) signal to blood pressure. These equations may contain coefficients that depend upon a patient's physiological characteristics as stored in encoder 42. In some embodiments, encoder 42 may include a memory or a coded resistor which stores one or more of the following types of information for communication to monitor 14: the types of sensors included in sensor unit 12; the wavelength or wavelengths of light used by an oximetry sensor when included in sensor unit 12; a signal threshold for each sensor in a sensor array; any other suitable information; or any combination thereof. Encoder 42 may also include information about the recalibration requirements of the sensors included in sensor unit 12, including any one of a nominal frequency of recalibration and preferred recalibration conditions.

In an embodiment, signals from sensor unit 12 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the Red LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, system 10 may include a stimulus drive, which may control when a stimulus is used to apply a signal to the patient, the response to which communicates information about the patient's physiological processes. Techniques for obtaining physiological measurements by inducing perturbations in a patient via a stimulus drive are described in more detail in co-pending, commonly assigned U.S. patent application Ser. No. 12/248,738, filed Oct. 9, 2008, entitled "SYSTEMS AND METHODS USING INDUCED PERTURBATION TO DETERMINE PHYSIOLOGICAL PARAMETERS," which is incorporated by reference herein in its entirety. It will be noted that embodiments of system 10 may include necessary control and drive circuitry suitable for the type of sensors included in sensor unit 12 (e.g., instead of or in addition to TPU 58 and/or light drive circuitry 60).

In an embodiment, microprocessor 48 may determine the patient's physiological parameters, such as blood pressure or blood oxygen saturation, using various algorithms and/or look-up tables based at least in part on the value of the received signals and/or data from sensor unit 12. For example, when sensor unit 12 includes an oximetry sensor, microprocessor 48 may generate an equation that represents empirical data associated with one or more patients that includes various blood pressure measurements associated with different areas under a pulse of a PPG signal. Signals corresponding to information about patient 40 may be transmitted from encoder 42 to a decoder 74. These signals may include, for example, encoded information relating to patient characteristics. Decoder 74 may translate these signals to enable the microprocessor to determine the thresholds based at least in part on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

Patient monitoring system 10 may also include calibration device 80. Although shown external to monitor 14 in the example of FIGS. 2(*a*) and 2(*b*), calibration device 80 may additionally or alternatively be internal to monitor 14. Calibration device 80 may be connected to internal bus 50 of monitor 14. As described above, reference measurements from calibration device 80 may be accessed by microprocessor 48 for use in calibrating the sensor measurements and determining physiological signals from the sensor signal and empirical data of one or more patients.

As discussed above, the signal from the patient can be degraded by noise, among other sources. One source of noise is electromagnetic coupling from other electronic instruments. Movement of the patient also introduces noise and affects the signal. For example, the contact between the sensor and the skin can be temporarily disrupted when movement causes either to move away from the skin. Another source of noise is ambient light that reaches the light detector in an oximetry system.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient and not the sensor site. Processing sensor signals may involve operations that reduce the amount of noise present in the signals or otherwise identify noise components in order to prevent them from affecting measurements of physiological parameters derived from the sensor signals.

In an embodiment, a signal may be transformed using a continuous wavelet transform. Information derived from the transform of the signal (i.e., in wavelet space) may be used in monitoring operations as discussed below.

The continuous wavelet transform of a signal x(t) in accordance with the present disclosure may be defined as $$T(a,b)=\frac{1}{\sqrt{a}}\int_{-\infty}^{+\infty}x(t)\psi^*\left(\frac{t-b}{a}\right)dt \tag{14}$$

where $\psi^*(t)$ is the complex conjugate of the wavelet function $\psi(t)$, a is the dilation parameter of the wavelet and b is the location parameter of the wavelet. The transform given by Eq. 14 may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale framework can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value in a spectral domain). As a further example, to reconstruct a temporal signal requires integrating twice, across time and scale, in the wavelet domain while, conversely, one integration across frequency is required to derive a temporal signal in a spectral domain. It is well known in the art that, in addition to or as an alternative to amplitude, parameters such as energy density, modulus, phase, among others, may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \quad (15)$$

where '||' is the modulus operator. The scalogram may be resealed for useful purposes. One common resealing is defined as $$S_R(a,b)=\frac{|T(a,b)|^2}{a} \quad (16)$$

and is useful for defining ridges in wavelet space when, for example, the Morlet wavelet is used. Ridges are defined as a locus of points of local maxima in the plane. A ridge associated with only the locus of points of local maxima in the plane is labeled a "maxima ridge." Also included as a definition of a ridge are paths displaced from the locus of the local maxima. Any other suitable definition of a ridge may be employed in the techniques described herein.

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and a multiplication of the result by $\sqrt{a}$.

In the discussion of the technology which follows herein, the term "scalogram" may be taken to include all suitable forms of resealing including, but not limited to, the original unsealed wavelet representation, linear resealing, any power of the modulus of the wavelet transform, or any other suitable resealing. In addition, for purposes of clarity and conciseness, the term "scalogram" shall be taken to mean the wavelet transform, T(a,b), itself or any part thereof. For example, the real part of the wavelet transform, the imaginary part of the wavelet transform, the phase of the wavelet transform, any other suitable part of the wavelet transform, or any combination thereof is intended to be conveyed by the term "scalogram."

A scale, which may be interpreted as a representative temporal period, may be converted to a characteristic frequency of the wavelet function. The characteristic frequency associated with a wavelet of arbitrary a scale is given by $$f=\frac{f_c}{a}, \quad (17)$$

where $f_c$ is the characteristic frequency of the mother wavelet (i.e., at a=1) and becomes a scaling constant, and f is the representative or characteristic frequency for the wavelet at arbitrary scale a.

Any suitable wavelet function may be used in connection with the present disclosure. One of the most commonly used complex wavelets, the Morlet wavelet, is defined as $$\psi(t)=\pi^{-1/4}\left(e^{i2\pi f_0 t}-e^{-(2\pi f_0)^2/2}\right)e^{-t^2/2}, \quad (18)$$

where $f_0$ is the central frequency of the mother wavelet. The second term in the parentheses is known as the correction term, as it corrects for the non-zero mean of the complex sinusoid within the Gaussian window. In practice, it becomes negligible for values of $f_0$>>0 and can be ignored, in which case, the Morlet wavelet can be written in a simpler form as $$\psi(t)=\frac{1}{\pi^{1/4}}e^{i2\pi f_0 t}e^{-t^2/2}. \quad (19)$$

This wavelet is a complex wave within a scaled Gaussian envelope. While both definitions of the Morlet wavelet are included herein, the function of Eq. 19 is not strictly a wavelet as it has a non-zero mean (i.e., the zero frequency term of its corresponding energy spectrum is non-zero). However, it will be recognized by those skilled in the art that Eq. 19 may be used in practice with $f_0$>>0 with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of physiological signals may be used to provide clinically useful information.

Pertinent repeating features in a signal give rise to a time-scale band in wavelet space or a resealed wavelet space. For example, the pulse component of a PPG signal produces a dominant band in wavelet space at or around the pulse frequency. FIGS. 3(*a*) and (*b*) show two views of an illustrative scalogram derived from a PPG signal, according to an embodiment. The figures show an example of the band caused by the pulse component in such a signal. The pulse band is located between the dashed lines in the plot of FIG. 3(*a*). The band is formed from a series of dominant coalescing features across the scalogram. This can be clearly seen as a raised band across the transform surface in FIG. 3(*b*) located within the region of scales indicated by the arrow in the plot (corresponding to 60 beats per minute). The maxima of this band with respect to scale is the ridge. The locus of the ridge is shown as a black curve on top of the band in FIG. 3(*b*). By employing a suitable resealing of the scalogram, such as that given in Eq. 16, the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary, and may vary in scale, amplitude, or both over time. FIG. 3(*c*) shows an illustrative schematic of a wavelet transform of a signal containing two pertinent components leading to two bands in the transform space, according to an embodiment. These bands are labeled band A and band B on the three-dimensional schematic of the wavelet surface. In an embodiment, a band ridge is defined as the locus of the peak values of these bands with respect to scale. For purposes of discussion, it may be assumed that band B contains the signal information of interest. Band B will be referred to as the "primary band." In addition, it may be assumed that the system from which the signal originates, and from which the transform is subsequently derived, exhibits some form of coupling between the signal components in band A and band B. When noise or other erroneous features are present in the signal with similar spectral characteristics of the features of band B, then the information within band B can become ambiguous (i.e., obscured, fragmented or missing). In this case, the ridge of band A (referred to herein as "ridge A") may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(*d*) show a schematic of the RAP and RSP signals associated with ridge A in FIG. 3(*c*). Below these RAP and RSP signals are schematics of a further wavelet decomposition of these newly derived signals. This secondary wavelet decomposition allows for information in the region of band B in FIG. 3(*c*) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(*c*)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts, remove noise, or any combination thereof. In one embodiment, there is an inverse continuous wavelet transform which allows the original signal to be recovered from its wavelet transform by integrating over all scales and locations, a and b, in accordance with $$x(t) = \frac{1}{C_g}\int_{-\infty}^{\infty}\int_{0}^{\infty} T(a, b)\frac{1}{\sqrt{a}}\psi\left(\frac{t-b}{a}\right)\frac{da\,db}{a^2}, \tag{20}$$

which may also be written as $$x(t) = \frac{1}{C_g}\int_{-\infty}^{\infty}\int_{0}^{\infty} T(a, b)\psi_{a,b}(t)\frac{da\,db}{a^2}. \tag{21}$$

where $C_g$ is a scalar value known as the admissibility constant. It is wavelet-type dependent and may be calculated in accordance with $$C_g = \int_{0}^{\infty}\frac{|\hat{\psi}(f)|^2}{f}df. \tag{22}$$

FIG. 3(*e*) is a flow diagram of illustrative steps that may be taken to perform an inverse continuous wavelet transform in accordance with the above discussion. An approximation to the inverse transform may be made by considering Eq. 20 to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(*f*) is a flow diagram of illustrative steps that may be taken to perform an approximation of an inverse continuous wavelet transform. It will be understood that any other suitable technique for performing an inverse continuous wavelet transform may be used in accordance with the present disclosure.

The present disclosure relates to methods and systems for using Lissajous figures in signal analysis and monitoring. As noted above, it will be understood that the present disclosure is applicable to any suitable signals and that physiological signals are described for illustrative purposes. The methods for using Lissajous figures in signal analysis and monitoring described in this disclosure may be implemented on a multitude of different systems and apparatuses through the use of human-readable or machine-readable information. For example, the methods described herein may be implemented using machine-readable computer code and executed on a computer system that is capable of reading the computer code. An exemplary system that is capable of signal analysis is depicted in FIG. 4.

Figure 4:
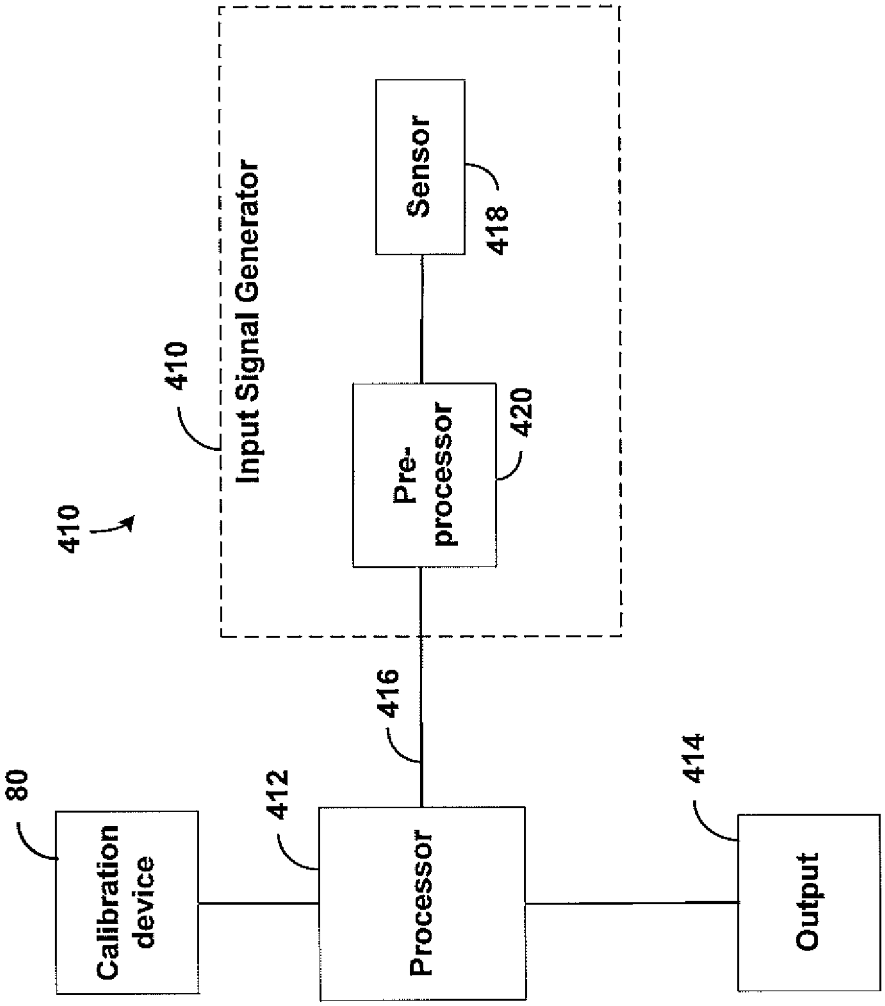
FIG. 4 is a block diagram of an illustrative signal processing system in accordance with an embodiment.

FIG. 4 is a block diagram of an illustrative processing system 400. In an embodiment, input signal generator 410 generates an input signal 416. As illustrated, input signal generator 410 includes pre-processor 420 coupled to sensor 418. It will be understood that input signal generator 410 may include any suitable signal source, signal generating data, signal generating equipment, or any combination thereof to produce signal 416. Signal 416 may be a single signal, or may be multiple signals transmitted over a single pathway or multiple pathways.

Pre-processor 420 may apply one or more signal processing techniques to the signal generated by sensor 418. For example, pre-processor 420 may apply a pre-determined transformation to the signal provided by the sensor 418 to produce an input signal 416 that can be appropriately interpreted by processor 412. Pre-processor 420 may also perform any of the following operations to the signal provided by the sensor 418: reshaping the signal for transmission; multiplexing the signal; modulating the signal onto carrier signals; compressing the signal; encoding the signal; and filtering the signal.

In an embodiment, signal 416 may include PPG signals at one or more characteristic frequencies, such as a Red PPG signal and an IR PPG signal. In an embodiment, signal 416 may include signals measured at one or more sites on a patient's body, for example, a patient's finger, toe, ear, arm, or any other body site. In an embodiment, signal 416 may include multiple types of signals (e.g., one or more of an acoustic signal, an optical signal, an electrical signal such as an EEG, EMG, EKG or EOG, a signal representing a blood pressure, a signal representing a heart rate).

In an embodiment of FIG. 4, signal 416 may be coupled to processor 412. Processor 412 may be any suitable software, firmware, and/or hardware, and/or combination thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may, for example, be configured of analog electronic components. Processor 412 may perform some or all of the calculations associated with the Lissajous figure derivation, Lissajous feature identification, measurement quality assessment, recalibration initiation and monitoring techniques of the present disclosure. For example, processor 412 may compute one or more of a similarity metric, a shape change metric and a noise metric based on a Lissajous figure. Processor 412 may compare an identified feature of a Lissajous figure to a threshold. Processor 412 may generate one or more suitable output signals, such as a measurement quality signal, a recalibration signal, and an information signal. Processor 412 may transmit an output signal to one or more suitable devices (e.g., calibration device 80 and/or display 20). Processor 412 may perform any suitable signal processing to filter signal 416, such as any suitable band-pass filtering, adaptive filtering, closed-loop filtering, and/or any other suitable filtering, and/or any combination thereof. Processor 412 may also receive input signals from additional sources (not shown). For example, processor 412 may receive an input signal containing information about treatments provided to the patient. Additional input signals may be used by processor 412 in any of the calculations or operations it performs in accordance with processing system 400.

Processor 412 may be coupled to calibration device 80. This coupling may take any of the forms described above with reference to calibration device 80 within system 10. For example, calibration device 80 may be a stand-alone device that may be in wireless communication with processor 412, or may be completely integrated within processor 412. Calibration device 80 may generate, or receive as an input, reference measurements for use in calibrating calculations. In an embodiment, processor 412 is capable of transmitting a command to calibration device 80 to initiate a recalibration procedure.

Processor 412 may be coupled to one or more memory devices (not shown) or incorporate one or more memory devices such as any suitable volatile memory device (e.g., RAM, registers, eta), non-volatile memory device (e.g., ROM, EPROM, magnetic storage device, optical storage device, flash memory, etc.), or both. In an embodiment, processor 412 may store physiological measurements or previously received data from signal 416 in a memory device for later retrieval. In an embodiment, processor 412 may store derived values, such as a Lissajous figure and/or one or more features of a Lissajous figure, in a memory device for later retrieval.

Processor 412 may identify one or more features of a Lissajous figure generated at least in part from signal 416. For example, processor 412 may identify within a Lissajous figure, one or more loops, one or more cycles, a similarity metric, a shape change metric, a noise metric, one or more principal components, a distance between one or more points, an area within a region of a Lissajous figure, any geometric characteristic of a Lissajous figure, or any combination thereof. Processor 412 may interpolate between points in signal 416 or between points in a Lissajous figure using any interpolation technique (e.g., zero-order hold, linear interpolation, and/or higher-order interpolation techniques).

In an embodiment, processor 412 may output a measurement quality signal via output 414, or through additional signal pathways not shown. A measurement quality signal may be output to any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof. In an embodiment, a measurement quality signal may include any one or more of a measurement quality value representative of current measurements, past measurements, a noise source, and a low measurement quality alert. In some embodiments, a measurement quality signal may be stored in a memory device or recorded in another physical form for future, further analysis. A measurement quality signal may be generated in response to a measurement quality assessment, as described in additional detail below. In an embodiment, processor 412 may transmit a command to calibration device 80 based at least in part on a measurement quality assessment.

It will be understood that system 400 may be incorporated into system 10 (FIGS. 2(*a*) and 2(*b*)) in which, for example, input signal generator 410 may be implemented as parts of sensor 12 (FIGS. 2(*a*) and 2(*b*)) and monitor 14 (FIGS. 2(*a*) and 2(*b*)) and processor 412 may be implemented as part of monitor 14 (FIGS. 2(*a*) and 2(*b*)). In some embodiments, portions of system 400 may be configured to be portable. For example, all or a part of system 400 may be embedded in a small, compact object carried with or attached to the patient (e.g., a watch, other piece of jewelry, or cellular telephone). In such embodiments, a wireless transceiver (not shown) may also be included in system 400 to enable wireless communication with other components of system 10 (FIGS. 2(*a*) and 2(*b*)). As such, system 10 (FIGS. 2(*a*) and 2(*b*)) may be part of a fully portable and continuous patient monitoring solution.

Figure 5:
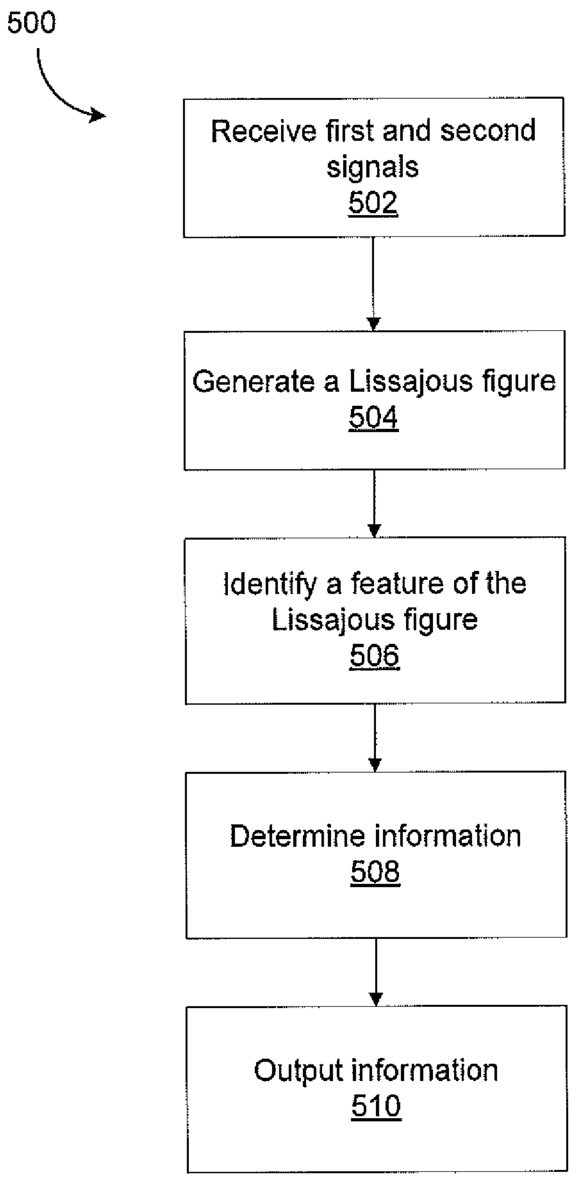
FIG. 5 is a flow diagram of illustrative steps involved in processing monitored signals using a Lissajous figure in accordance with an embodiment.

FIG. 5 is a flow diagram 500 of illustrative steps involved in processing monitored signals using a Lissajous figure in accordance with an embodiment. The steps of flow diagram 500 may be performed by processor 412 (FIG. 4), or may be performed by any suitable processing device communicatively coupled to monitor 14 (FIGS. 2(*a*) and 2(*b*)). The steps of flow diagram 500 may be performed by a digital processing device, or implemented in analog hardware. In an embodiment, the steps of flow diagram 500 may be performed by a continuous, non-invasive blood pressure (CNIBP) monitoring system. It will be noted that the steps of flow diagram 500 may be performed in any suitable order, and certain steps may be omitted entirely.

The steps of flow diagram 500 may be executed over a sliding window of a signal. For example, the steps of flow diagram 500 may involve analyzing the previous N samples of the signal, or the samples of the signal received in the previous T units of time. The length of the sliding window over which the steps of flow diagram 500 are executed may be fixed or dynamic. In an embodiment, the length of the sliding window may be based at least in part on the noise content of a signal. For example, the length of the sliding window may increase with decreasing measurement quality and/or increasing noise, as may be determined by a measurement quality assessment and/or a noise assessment. Examples of illustrative measurement quality and noise assessment techniques are described in detail below.

At step 502, first and second signals may be received. A signal (e.g., a PPG signal) may be received from any suitable source (e.g., patient 40 of FIG. 2(*b*)) using any suitable technique. A received signal may be generated by sensor unit 12 and/or sensor unit 13 (FIG. 2(*a*)), which may itself include any of the number of physiological sensors described herein. A received signal may be signal 416 (FIG. 4), which may be generated by a pre-processor 420 (FIG. 4) coupled between processor 412 (FIG. 4) and sensor 418 (FIG. 4). A single received signal may include multiple signals (e.g., first and second signals), for example, in the form of a sequence or collection of signal segments, a multi-dimensional vector signal or a frequency- or time-multiplexed signal, Additionally, a signal received at step 502 may be a derived signal generated internally to processor 412 (FIG. 4). Accordingly, a received signal may be based at least in part on a filtered version of a signal 416 (FIG. 4), or a combination of multiple signals. For example, a received signal may be a ratio of two signals. A received signal may be a transformation of signal 416 (FIG. 4), such as a continuous wavelet transformation of signal 416 (FIG. 4). A received signal may be based at least in part on past values of a signal, such as signal 416 (FIG. 4), which may be retrieved by processor 412 (FIG. 4) from a memory such as a buffer memory or RAM 54 (FIG. 2(*b*)). A received signal may be a manipulated signal, such as one or more time derivatives of signal 416 (FIG. 4).

First and second PPG signals may be received as input signal 416 (FIG. 4). In an embodiment, a first signal may be a Red PPG signal, and a second signal may be an IR PPG signal. In an embodiment, first and second signals may be different types of signals (e.g., a blood pressure signal and a pulse rate signal). In an embodiment, first and second signals may be obtained by first and second sensors, respectively, located at approximately the same body site. In an embodiment, first and second signals may be obtained by first and second sensors, respectively, located at different body sites. For example, first and second signals may be electronic signals from pulse oximetry sensors located at two different body sites. In an embodiment, one or more of the first and second received signals is a time derivative of a PPG signal transmitted, for example, as signal 416 (FIG. 4).

In an embodiment, more than two signals may be received at step 502. For example, PPG signals at three or more frequencies may be obtained at step 502. It will be noted that the steps of flow diagram 500 may be applied to any number of received signals in accordance with the techniques described herein. In an embodiment, a physiological signal (such as a PPG signal) may be obtained from more than two body sites. For example, signals may be recorded from three body sites (e.g., ear, finger and toe) and triangulated to produce improved physiological measurements. In such embodiments, a three-dimensional Lissajous figure may be employed to identify and quantify noise and changing signal characteristics.

In an embodiment, one or more of the first and second signals received at step 502 may be transformed. A transformation may occur in conjunction with the receiving at step 502, or after the signals are received at step 502. In an embodiment, processor 412 (FIG. 4) may transform the signal into any suitable domain, for example, a Fourier, wavelet, spectral, scale, time, time-spectral, time-scale domain, or any transform space. A transformation may be performed by any one or more of the transformation techniques described herein, including a continuous wavelet transformation. A transformation may be performed by any suitable processing device, such as processor 412 (FIG. 4) and/or microprocessor 48 (FIG. 2(*b*)), which may each be a general-purpose computing device or a specialized processor. A transformation may be performed by a separate, dedicated device. Processor 412 (FIG. 4) may further transform the original and/or transformed signals into any suitable domain. In an embodiment, a transformation may be based at least in part on a continuous wavelet transformation. For example, a PPG signal may be transformed using a continuous wavelet transform as described above with reference to FIG. 3(*c*). In an embodiment, a transformation may include performing a continuous wavelet transform for one or more PPG signals received, for example, at step 502, including a PPG signal obtained at a first body site, a PPG signal obtained at a second body site, or any combination of signals.

In an embodiment, a scalogram may be generated as part of a transformation of one or more of the signals received at step 502. A scalogram may be generated by any of the techniques described herein, including those described above with reference to FIGS. 3(*a*) and 3(*b*). For example, processor 412 (FIG. 4) or microprocessor 48 (FIG. 2(*b*)) may perform the calculations associated with the continuous wavelet transform of a signal and the derivation of a corresponding scalogram. In an embodiment, a scalogram may be based on any one or more features of a transformed signal. For example, a scalogram may represent the real part of a transformed signal, the imaginary part of a transformed signal, the modulus of a transformed signal, any other suitable feature of the transformed signal, or any combination thereof. In an embodiment, one or more of the signals received at step 502 may represent a scalogram of a signal. For example, a first received signal may be a continuous wavelet transformation of a Red PPG signal, and a second received signal may be a continuous wavelet transformation of an IR PPG signal.

In an embodiment, a scalogram may only be calculated at previously-selected scales of interest. For example, the values of a scalogram representation at a first particular scale may be derived for the first signal received at step 502, while the values of a scalogram representation at a second particular scale may be derived for the second signal received at step 502. The first and second particular scales may be the same, or may be different. As is discussed in additional detail below, multiple Lissajous figures may be derived based on first and second received signals, each Lissajous figure representing scalogram values at particular scales for each of the first and second received signals. In an embodiment, processor 412

(FIG. 4) may identify one or more ridges of a scalogram representation of a signal received at step 502.

In an embodiment, pre- or post-processing techniques may be applied to one or more of the first and second signals received at step 502. These techniques may include any one or more of the following: compressing, multiplexing, modulating, up-sampling, down-sampling, smoothing, taking a median or other statistic of the received signal, removing erroneous regions of the received signal, or any combination thereof. In an embodiment, a normalization step may be performed which divides the magnitude of the received signal by a value. This value may be based on at least one of the maximum of the received signal, the minimum of the received signal and the mean of the received signal. In an embodiment, a signal received at step 502 may be normalized by dividing the signal by a DC component. In an embodiment, a signal received at step 502 may be normalized by dividing the signal by the standard deviation of the signal computed over a time window.

In an embodiment, one or more of the first and second signals received at step 502 may be manipulated by calculating one or more time derivatives. A time derivative may be calculated by input signal generator 410 (FIG. 4) (alone or in conjunction with additional pre-processing steps), or may be calculated by processor 412 (FIG. 4). In an embodiment, a time derivative may be calculated by any of a number of derivative/gradient determination and approximation techniques, including those suitable for sampled data (e.g., forward difference, backward difference, central difference, higher-order methods, and any automatic differentiation method).

In an embodiment, one or more of the first and second signals received at step 502 may be time-shifted. A time-shifting operation may be performed to bring one or more signals into alignment, to minimize the phase difference between periodic signals, to correct for a known delay, or any combination thereof. Such a time shift may be performed, for example, by computing a correlation across time between two signals then shifting one or more of the two signals based at least in part on a time-shift of maximum correlation. In an embodiment, a time-shifting operation may be performed based on a differential pulse transit time (DPTT) between signals measured at two different locations. For example, first and second signals may be detected by sensors (such as sensors included in sensor units 12 and 13 of FIG. 2(*a*)) located at two different sites on a patient's body, and may correspond to a physiological phenomenon arising at a third body site. An illustrative example of such signals may be two oximetry sensors detecting PPG signals at two body sites, wherein such signals may arise from pulsatile circulatory waves originating at the heart. A DPTT may be determined by any of a number of pulse identification and/or delay identification techniques, or may be derived from empirical data or theoretical models.

In an embodiment, one or more of the first and second signals received at step 502 may be filtered using any suitable filtering technique. For example, a signal received at sensor 12 (FIGS. 2(*a*) and 2(*b*)) may be filtered by a low pass filter 68 (FIG. 2(*b*)) prior to undergoing additional processing at microprocessor 48 (FIG. 2(*b*)) within patient monitoring system 10 (FIGS. 2(*a*) and 2(*b*)). In an embodiment, a signal received at step 502 may be high or band pass filtered to remove low frequencies. Such a filter may be, for example, a derivative filter. In an embodiment, a signal received at step 502 may be filtered to remove a DC component. In an embodiment, a PPG signal may be band-pass filtered to pass frequencies in the approximate range 0.5-3 Hz. In an embodiment, the cutoff frequencies of a filter may be chosen based on the frequency response of the hardware platform underlying patient monitoring system 10 (FIGS. 2(*a*) and 2(*b*)). The low pass filter 68 (FIG. 2(*b*)) may selectively remove frequencies that may later be ignored by the transformation, which may advantageously reduce computational time and memory requirements.

Different operations, which may include transformation, manipulation and/or filtering techniques, may be applied to any one or more of the first and second signals received at step 502 and/or any components of a multi-component signal. For example, different operations may be applied to a signal taken from a first body site and a signal taken from a second body site. As described above, in an embodiment, a Lissajous figure may represent a time derivative of a first signal and a non-time derivative of a second signal. Taking a derivative of a signal may selectively emphasize the signal's high frequency components. In an embodiment, a first monitored signal may be passed through a high-pass filter and a second monitored signal may not be passed through a high-pass filter. Using these two signals to generate a Lissajous figure may result in a Lissajous figure similar to one that would be obtained by using a time derivative of the first monitored signal and a non-time derivative of the second monitored signal.

Any of the operations described herein may be applied to a portion or portions of a received signal. An operation may be broken into one or more stages performed by one or more devices within signal processing system 400 of FIG. 4 (which may itself be a part of patient monitoring system 10 of FIGS. 2(*a*) and 2(*b*)). For example, a filtering technique may be applied by input signal generator 410 (FIG. 4) prior to passing the resulting input signal 416 (FIG. 4) to processor 412 (FIG. 4), where it may undergo a transformation and/or the calculation of a time derivative. Embodiments of the steps of flow diagram 500 include any of the operations described herein performed in any suitable order.

Any number of computational and/or optimization techniques may be performed in conjunction with the techniques described herein. For example, any known information regarding the physiological status of the patient may be stored in memory (e.g., ROM 52 or RAM 54 of FIG. 2(*b*)). Such known information may be keyed to the characteristics of the patient, which may be input via user inputs 56 (FIG. 2(*b*)) and used by monitor 14 (FIG. 2(*b*)) to, for example, query a lookup table and retrieve the appropriate information. Additionally, any of the calculations and computations described herein may be optimized for a particular hardware implementation, which may involve implementing any one or more of a pipelining protocol, a distributed algorithm, a memory management algorithm, or any suitable optimization technique.

At step 504, a Lissajous figure may be generated based at least in part on the first and second signals received at step 502. A Lissajous figure may include a comparison between the first and second signals. The comparison may take the form of a plot in two or more dimensions, with the first signal plotted on a first axis and the second signal plotted on a second axis. In an embodiment, the Lissajous figure generated at step 504 is generated in three or more dimensions. Each of the axes in a Lissajous figure calculated at step 504 may represent one or more of: a received signal (e.g., the first and/or second signals received at step 502), a transformation of a received signal, a mathematical manipulation of a received signal, a signal derived from a received signal, a reference signal, and any combination thereof. In an embodiment, a Lissajous figure may be based at least in part on one or more PPG signals measured at a patient. In an embodiment, a Lissajous figure may be based on a PPG signal measured at a first body site and a PPG signal measured at a second body site, and may include a two-dimensional plot in which the PPG signal at the first body site is represented by a first axis and the PPG signal at the second body site is represented by a second axis. In an embodiment, a Lissajous figure may be based on a Red PPG signal and an IR PPG signal, and may include a two-dimensional plot in which the Red PPG signal is represented by a first axis and the IR PPG signal is represented by a second axis. In an embodiment, a Lissajous figure may be displayed for a user in any manner described herein, including via displays 20 and 28 (FIG. 2(*a*)). A Lissajous figure may also be recorded to a memory device (e.g., RAM 54 of FIG. 2(*b*) or a remote storage device) or a physical medium such as a print-out.

In an embodiment, a Lissajous figure may be based at least in part on transformations of one or more PPG signals taken from a patient. In an embodiment, a Lissajous figure may be based on a feature of a transformation of a first signal and a feature of a transformation of a second signal. First and second signals may be, for example, PPG signals at different frequencies, PPG signals measured at different body sites, any two different signals (which may include one or more time derivative signals), or any combination thereof. In an embodiment, a feature of a transform of a signal may be based on one or more ridges in a scalogram representation of the signal. For example, one of the first and second signals represented by a Lissajous figure may be based on a scalogram ridge or a projection of a scalogram ridge.

In an embodiment, a Lissajous figure may be based at least in part on the values of a scalogram at a particular scale. A set of scalogram values may be calculated for each of a first scalogram (representing a first signal) and a second scalogram (representing a second signal), and for one or more scales. For each scale, the set of scalogram values for the first scalogram may be plotted against the set of scalogram values for the second scalogram in a two-dimensional plot. Any one or more of these two-dimensional plots (each corresponding to a particular scale) may serve as a Lissajous figure to which the techniques described herein may be applied. Multiple such two-dimensional plots (each corresponding to a particular scale) may be arranged along a scale axis to form a three-dimensional plot. This three-dimensional plot may serve as a three-dimensional Lissajous figure to which the techniques disclosed herein may be applied. Additional Lissajous figures may be derived from such a three-dimensional Lissajous figure. For example, a two-dimensional Lissajous figure may be derived by projecting a region of any three-dimensional Lissajous figure onto a two-dimensional plane. The techniques disclosed herein may be applied to this two-dimensional Lissajous figure.

Once a Lissajous figure is generated at step 504, a feature of the Lissajous figure may be identified at step 506. In an embodiment, identifying a feature of a Lissajous figure at step 506 may include generating one or more statistics representing a relationship between the first and second signals. For example, identifying a feature of a Lissajous figure may include determining a best-fit curve, performing a principal component analysis, analyzing a trajectory, or any combination thereof. Step 506 may include identifying two or more features of a Lissajous figure generated at step 504, and may include combining multiple identified features or determining additional features based at least in part on the multiple identified features.

Figure 6A:
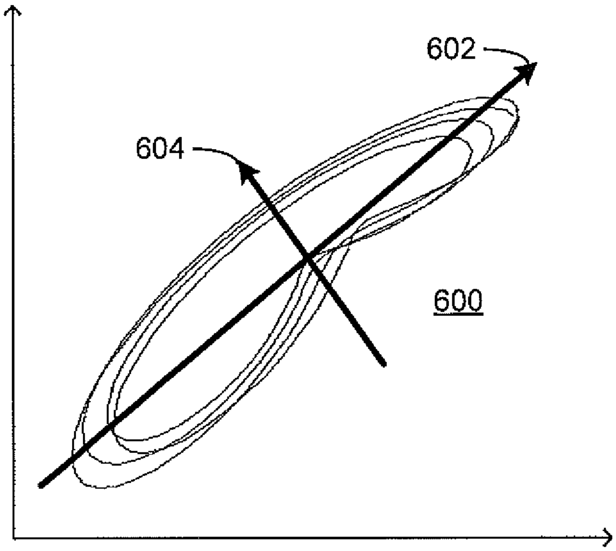
FIGS. 6(*a*) and 6(*b*) illustrate examples of features of Lissajous figures in accordance with an embodiment.
Figure 6B:
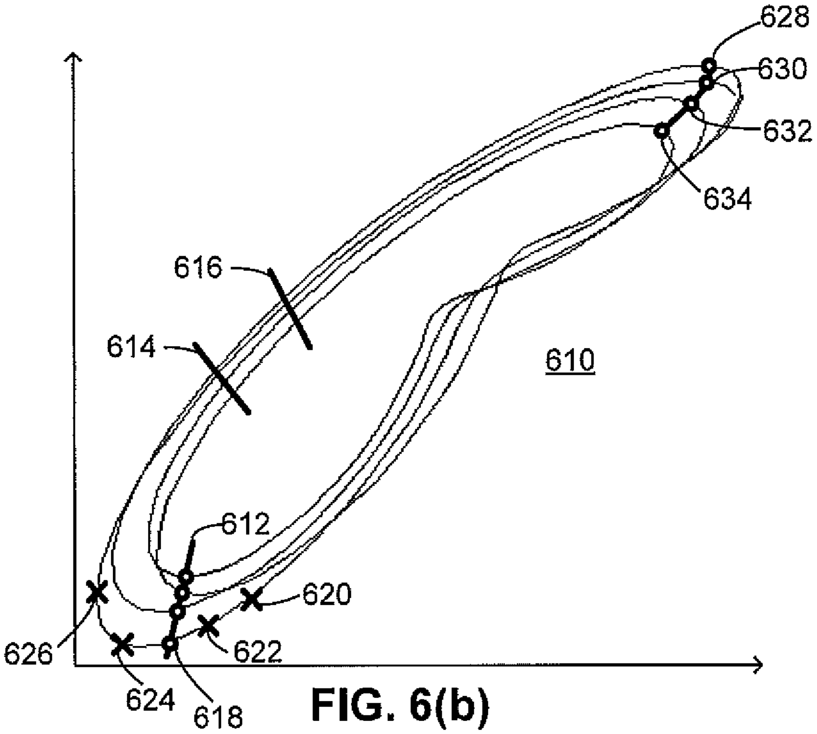

In an embodiment, a feature of a Lissajous figure identified at step 506 may include a similarity metric. A similarity metric may assess the similarity of the two or more signals represented by the Lissajous figure generated at step 504. In an embodiment, a similarity metric may be any measure of the deviation of a Lissajous figure from a straight line (in two or more dimensions). In an embodiment, a similarity metric may include any one or more the following illustrative similarity metrics:

1. A variation of points in a Lissajous figure around one or more principal components of the Lissajous figure. A principal component analysis, performed in accordance with known techniques, may determine one or more principal components of the points of a Lissajous figure. For example, a three-dimensional Lissajous figure may allow three principal components to be determined. A principal component may indicate a direction of maximum variability within the data underlying the Lissajous figure. For example, FIG. 6(*a*) depicts an illustrative example of two-dimensional Lissajous figure 600 with first principal component 602 and second principal component 604. The variation of the Lissajous figure around (e.g., away from) one or more principal components may indicate an extent to which the Lissajous figure deviates from an n-dimensional plane (i.e., a line when one principal component is considered, a two-dimensional plane when two principal components are considered, etc.). The variation of points around one or more principal components may be determined according to any variability measure, including a variance, a standard deviation, a higher-order moment, a maximum deviation, a median deviation, or any combination thereof. In an embodiment, a similarity metric may include the variance of the points in a Lissajous figure around a first (or dominant) principal component. Any suitable technique for component analysis and/or dimensionality reduction may be used, including eigenvector-based techniques, factor analysis, and any suitable non-linear techniques.

2. An area/volume enclosed by one or more trajectories in a Lissajous figure. In the absence of noise, a Lissajous figure in which the underlying signals are similar (which may include compensating for a time delay) may exhibit low variance around the principal component, reflecting a linear relationship between the signals. In the presence of noise, trajectories of such a Lissajous figure may vary from a strictly linear relationship, and a measurement of the area/volume enclosed by one or more trajectories of the Lissajous figure may provide a measure of this variation from linearity. The area/volume enclosed by one or more trajectories in a Lissajous figure may be used as a similarity metric for any Lissajous figure representing two or more signals (e.g., Red and IR PPG signals measured at a single body site, multiple PPG signals measured at multiple body sites). The area/volume of one or more trajectories of a Lissajous figure may be calculated and/or approximated by any suitable known technique.

3. A hypothesis test result on a linear form for the Lissajous figure. In an embodiment, a hypothesis test may be performed to determine the likelihood that the signals underlying a Lissajous figure are related linearly. As is understood by one skilled in the art, a hypothesis test may depend on prior probabilities, which may be determined from previously collected data (e.g., from the same patient or other patients in a clinical setting), from theoretical models of a process underlying the signals represented by the Lissajous figure, measurements of environmental characteristics (e.g., the distribution of interfering noise), any other suitable information source, or any combination thereof. In an embodiment, a similarity metric based on a hypothesis test may take values of "linear" and "non-linear." In an embodiment, a similarity metric based on a hypothesis test may take values in the interval [0, 1], representing a probability and/or confidence that the Lissajous figure has a linear form.

In an embodiment, a feature of a Lissajous figure identified at step 506 may include a shape change metric. A shape change metric may provide an assessment of a change in the form of a Lissajous figure. As discussed above, some signals of interest, including some physiological signals such as PPG signals, may be periodic, In these embodiments, a Lissajous figure based at least in part on the periodic signal may exhibit a cyclic or repeating trajectory. For example, illustrative Lissajous figure 610 of FIG. 6(*b*) may include approximately four cycles. A cyclic trajectory need not be (and most likely, will not be) identical from cycle to cycle due to noise, measurement drift, variations in sensor function, and changes in the underlying signals which may arise from changes in patient condition. Features of a Lissajous figure which indicate a change in morphology of the Lissajous figure from cycle to cycle may indicate a change in patient condition, a need for recalibration of the measurement system, or other monitoring condition. A shape change metric may assess a difference between one or more cycles in a current Lissajous figure. In an embodiment, a shape change metric may include any one or more of the following illustrative shape change metrics:

1. A measure based on distances between points in a "slice" of a Lissajous figure. Slices of Lissajous figure 610 are indicated by line segments 612, 614, and 616 in FIG. 6(*b*), each of which intersects multiple cycles within the Lissajous figure. Points in the slice are the intersection points of the Lissajous figure and the line segment, as illustrated by the four points indicated as circles (including point 618) along line segment 612. In an embodiment, a continuous or approximately continuous trajectory of a Lissajous figure may need to be interpolated from discrete points which are the samples of the signals represented by the Lissajous figure (e.g., as produced by any digital measuring or processing device). For example, the point 618 may need to be interpolated from one or more data points in Lissajous figure 610, such as data points 620, 622, 624 and 626. In an embodiment, a shape change metric may be based on one or more of: the distance between each point and its closest neighbor along the slice; the distance between each point and its furthest neighbor along the slice; and the distance between each point in the slice and the point in the slice which is associated with a subsequent cycle, or a cycle an integer number of cycles ahead or behind. In an embodiment, a shape change metric may be any statistic of one or more of such distances, including an average distance, a median distance, a minimum distance and a maximum distance. For example, a shape change metric may include summing the distances to nearest points along the slice, then dividing by the number of points. In any of the embodiments described herein, the term "distance" may refer to any suitable distance metric (e.g., a Euclidean distance).

2. A measure based on distances between closest points in subsequent cycles in a Lissajous figure. In a cyclic Lissajous figure, each point may be associated with a cycle. It will be noted that there may be many such associations for each point in a cyclic Lissajous figure, but that points corresponding to different cycles may nevertheless be distinguishable. For example, points 628, 630, 632 and 634 of Lissajous figure 610 of FIG. 6(*b*) may be associated with four different cycles. In an embodiment, a shape change metric may be based on identifying, for a first point associated with a cycle, a second point associated with a different cycle which is closest to the first point. For example, in FIG. 6(*b*), point 630 may be the closest point associated with a different cycle to point 628, point 632 may be the closest point associated with a different cycle to point 630, and point 634 may be the closest point associated with a different cycle to point 632. As discussed above, a continuous or approximately continuous trajectory of a Lissajous figure may need to be interpolated from discrete points which are the samples of the signals represented by the Lissajous figure (e.g., as produced by any digital measuring or processing device). In an embodiment, a shape change metric may be based one or more of: the smallest distance between each point and a point in the trajectory corresponding to a different cycle, and the smallest distance between each point and a point in the trajectory corresponding to a subsequent cycle. In an embodiment, a shape change metric may be any statistic of one or more of such distances, including an average distance, a median distance, a minimum distance and a maximum distance. For example, a shape change metric may include summing the distances to closest points, then dividing by the number of points.

3. A measure based on a change in one or more principal components between cycles. For each set of one or more cycles in a Lissajous figure, a principal component analysis may be performed and one or more principal components may be identified. Such principal components may be compared between sets of one or more cycles to determine changes in shape between sets. For example, a first principal component may change in both direction and magnitude between one cycle and a subsequent cycle. A measure of such a change may serve to quantify changes in shape of a Lissajous figure between sets of cycles.

4. A measure based on area/volume between cycles in a Lissajous figure. In an embodiment, the area/volume approximately enclosed within a cycle of a Lissajous figure may be compared to the area/volume approximately enclosed within another cycle of a Lissajous figure. In an embodiment, a shape change metric may be based on the area/volume of a region enclosed by a first cycle of a Lissajous figure and not enclosed by a second cycle of a Lissajous figure (e.g., the set difference of the enclosed areas). Such a measure may also be based on first and second sets of cycles as described above.

In an embodiment, a feature of a Lissajous figure identified at step 506 may include a noise metric. A noise metric may characterize any source of interference or disruption affecting one or more of the signals represented by the Lissajous figure. A noise metric be based on any of the previously-described metrics, such as any of the similarity and shape change metrics described above. In an embodiment, a noise metric may include any one or more of the following illustrative noise metrics:

1. A comparison between variations around one or more principal components. As described above, one or more principal components of a Lissajous figure may be calculated in accordance with any suitable technique. In an embodiment, a noise metric may be based at least in part on a comparison between a variation around a first principal component and a variation around a second principal component. For example, a noise metric may be based at least in part on a ratio between a variance around a second principal component and a variance around a first principal component.

2. An angle of a principal component. In an embodiment, the first and second signals received at step 502 may each be normalized by dividing each by a fixed value. This fixed value may be different for each of the first and second signals. For example, each signal may be normalized by dividing by a measure of the variability of the signal over a time window (e.g., the standard deviation). Once the signals have been normalized, a Lissajous figure may be calculated and a principal component analysis may be performed as described above. In an embodiment, a noise metric measures the angle of the first principal component of the Lissajous figure. Deviations of this angle from 45 degrees may indicate a corruption of one or both of the first and second received signals, and may indicate the presence of noise.

3. A mean distance of points in a Lissajous figure from a reference curve. A reference curve may be a best-fit line, a principal component, a best fit higher order curve, or any suitable reference curve. In an embodiment, a large mean distance of the points in a Lissajous figure from a best-fit line or principal component may indicate a difference in shape between the two or more signals upon which the Lissajous figure is based, and thus may indicate noise in one or more of the signals.

It will be noted that the categories of metrics described above, such as "similarity," "shape change" and "noise" are included for clarity of presentation, and that any feature or metric described herein may be used for any suitable signal monitoring application. For example, the similarity metrics described above may be used to quantify noise in a signal monitoring system, including the variance of a Lissajous figure around a first principal component and the area enclosed by one or more cycles of a Lissajous figure.

In an embodiment, any of the metrics described herein, including those listed above, may include a comparison between a Lissajous figure and an archetypal Lissajous figure. An archetypal Lissajous figure may serve as a reference Lissajous figure, and may represent an expected shape of the Lissajous figure, an average shape of the Lissajous figure, an ideal shape of the Lissajous figure, or a worst-case shape of a Lissajous figure. An archetypal Lissajous figure may be calculated on a patient-by-patient basis (based on, for example, patient characteristics), determined from a population average, predicted by a theoretical model, or generated at regular intervals (such as recalibrations). An archetypal Lissajous figure may be generated by combining one or more previously-determined Lissajous figures, or by combining several cycles within a single Lissajous figure. In an embodiment, an archetypal Lissajous figure may be generated by ensemble averaging multiple Lissajous figures taken over a period of time. Calculating an ensemble average may involve identifying separate cycles within the Lissajous figure prior to combining the separate cycles, for which any suitable cycle identification technique may be used. Cycles may be identified by examining the signals represented in the Lissajous figure, for example, to delineate pulses in the signals. An archetypal Lissajous figure may be stored, for example, in ROM 52 or RAM 54 (FIG. 2(*b*).

In an embodiment, any of the features described herein, including the similarity, shape change, and noise metrics described above, may be identified in local regions of a Lissajous figure and compared across regions. For example, a shape change metric that is based on a measure of distances between closest points in subsequent cycles may be calculated in one or more regions of a Lissajous figure. Any two or more local features of a Lissajous figure may be combined to identify a global feature of the Lissajous figure. For example, a global feature may be the maximum, minimum, median, or average value of local features (such as shape change metrics based on a slice, or based on closest points). In an embodiment, any suitable feature described herein may be averaged over the entire Lissajous figure to obtain a mean estimate of the spread of Lissajous figure trajectories.

Two or more local features may be compared to each other to characterize the location of changes in a Lissajous figure. In an embodiment, features in one local region of a Lissajous figure may be compared to features in a second local region of the Lissajous figure to determine a relationship between features in each region. For example, the relative size (e.g., area, perimeter) of a notch loop in a Lissajous figure as compared to a larger loop (e.g., a "pulse" loop) may indicate an augmentation index of a pulse wave.

In an embodiment, a feature of a Lissajous figure may be monitored over time. For example, any one of the features or metrics described herein may be plotted against time (e.g., continuously, cycle to cycle, or on a periodic or aperiodic basis). Tracking one or more of the features over time may indicate long and/or short-term changes in the Lissajous figure, and may itself be a feature identified at step 506. Local features of Lissajous figures may be monitored over time. For example, a feature value of a Lissajous figure computed in a first local region may be plotted against time, and compared to a second plot of local feature values against time computed at a second, later time. In an embodiment, a change in size of a "notch loop," as discussed herein, may indicate a change in a patient's peripheral resistance and/or vasotone.

Once a feature of a Lissajous figure is identified at step 506 of flow diagram 500 of FIG. 5, information may be determined from at least the identified feature at step 508. In an embodiment, the information may be physiological information derived from a comparison of physiological signals. In an embodiment, the steps of flow diagram 500 may be carried out by a continuous, non-invasive blood pressure (CNIBP) monitoring system, and the information determined at step 508 may be relevant to a blood pressure estimate based at least in part on PPG signals from multiple body sites. For example, a blood pressure estimate may be based on multiple estimates of differential pulse transit time (DPTT), taken at multiple time instances, determined from multiple received PPG signals. A feature of a Lissajous figure representing two or more of the received PPG signals may correspond, for example, to a change in DPTT at a current time instance due to a physiological change (e.g., a change in patient posture) other than a change in patient blood pressure. At step 508, then, the CNIBP system may ignore or re-weight the DPTT estimate at the current time instance (e.g., associated with a period of patient posture change) when computing a blood pressure estimate, or may indicate the change in patient posture to the patient or care provider via a display, such as display 28 (FIG. 2(*a*)). In an embodiment, the information may be a measurement quality assessment. In an embodiment, the information may be a recalibration assessment. The information determined at step 508 may be quantitative or qualitative, and may be the result of applying a predictive model such as a neural network to the Lissajous figure.

In an embodiment, a predictive computational model may be used to determine information at step 508. For example, a predictive computational model may determine one or more of: estimates of a patient's current physiological status, estimates of a physiological parameter, estimates of a patient's prognosis, a proposed explanation for a change in a Lissajous figure, and a proposed source of noise. A predictive computational model, executed, for example, by processor 412 (FIG. 4), may be based in part on at least one of the following data sources: the received signal (e.g., input signal 416 of FIG. 4); additional signals (e.g., physiological and/or environmental signals); a Lissajous figure representing one or more received signals; patient characteristics; historical data of the patient or other patients; and computational or statistical models of physiological processes. Processor 412 (FIG. 4) may retrieve any of these data sources from memory such as ROM 52 or RAM 54 (FIG. 2(*b*)), from an external memory device, or from a remote memory device. The structure of a predictive computational model may, for example, be based on any of the following models: a neural network, a Bayesian classifier, and a clustering algorithm. In an embodiment, processor 412 (FIG. 4) may develop a predictive neural network for noise assessment based at least in part on historical data from the given patient and/or other patients. In some embodiments, processor 412 may implement the predictive computational model as a hypothesis test. Processor 412 (FIG. 4) may continually refine or augment the predictive computational model as new data and/or signals are received. The predictive model may also be refined based on feedback from the patient or care provider received through the user inputs 56 (FIG. 2(*b*)). Other predictive frameworks may include rule-based systems and adaptive rule-based systems such as propositional logic, predicate calculus, modal logic, non-monotonic logic and fuzzy logic.

At step 510, the information determined at step 508 may be output to an output device. Information may be output through a graphical representation, quantitative representation, qualitative representation, or combination of representations via output 414 (FIG. 4) and may be controlled by processor 412 (FIG. 4). In an embodiment, output 414 (FIG. 4) may transmit physiological information by any means and through any format useful for informing a patient, a care provider, or a third party, of a patient's status and may involve recording the physiological information to a storage medium. Quantitative and/or qualitative information provided by output 414 (FIG. 4) may be displayed on a display: for example, on display 28 (FIG. 2(*a*)). A graphical representation may be displayed in one, two, or more dimensions and may be fixed or change with time. A graphical representation may be further enhanced by changes in color, pattern, or any other visual representation. Output 414 (FIG. 4) may communicate the information by performing at least one of the following: presenting a screen on a display; presenting a message on a display; producing a tone or sound; changing a color of a display or a light source; producing a vibration; and sending an electronic message. Output 414 (FIG. 4) may perform any of these actions in a device close to a patient, or at a mobile or remote monitoring device as described previously. In an embodiment, output 414 (FIG. 4) may produce a continuous tone or beeping whose frequency changes in response to changes in a process of interest, such as a physiological process. In an embodiment, output 414 (FIG. 4) may produce a colored or flashing light that changes in response to changes in a physiological process of interest.

In an embodiment, the information output at step 510 may include information about measurement quality. Such information may be output as a measurement quality signal produced by processor 412 (FIG. 4) and transmitted via output 414 (FIG. 4) as described above. In an embodiment, the information output at step 510 may include a recalibration signal. As described above, a recalibration signal may initiate the calibration of monitor 14 (FIGS. 2(*a*) and 2(*b*)) or may communicate recalibration information (e.g., via a recalibration schedule). The recalibration signal may be transmitted to calibration device 80 (FIG. 4) from processor 412 (FIG. 4).

After or during the output of information at step 510, the steps of flow diagram 500 may be repeated. New first and second signals may be received, or the information determination may continue on another portion of one or more of the first and second received signal(s). In an embodiment, processor 412 (FIG. 4) may continuously or periodically perform steps 502-510 and update the information (a g, as the patient's condition changes). The process may repeat indefinitely, until there is a command to stop the monitoring and/or until some detected event occurs that is designated to halt the monitoring process. For example, it may be desirable to halt a monitoring process when a detected noise has become too great, a measurement quality has become too low, or, in a patient monitoring setting, when a patient has undergone a change in condition that can no longer be sufficiently well-monitored in a current monitoring configuration. In an embodiment, processor 412 (FIG. 4) performs the steps of flow diagram 500 at a prompt from a care provider via user inputs 56 (FIG. 2(*b*)). In an embodiment, processor 412 (FIG. 4) may perform the steps of flow diagram 500 at intervals that change according to patient status. For example, the steps of flow diagram 500 may be performed more often when a patient is undergoing rapid changes in physiological condition, and performed less often as the patient's condition stabilizes.

Figure 7:
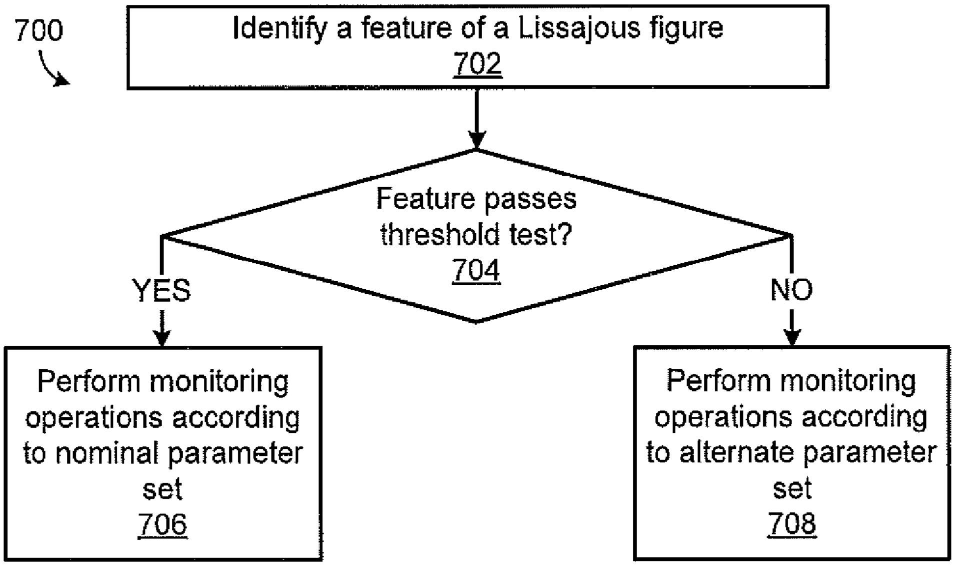
FIG. 7 is a flow diagram of illustrative steps involved in signal monitoring using a Lissajous figure in accordance with an embodiment.

FIG. 7 is a flow diagram 700 of illustrative steps involved in signal monitoring using a Lissajous figure. The steps of flow diagram 700 may be performed by processor 412 (FIG. 4), or may be performed by any suitable processing device communicatively coupled to monitor 14 (FIGS. 2(*a*) and 2(*b*)). The steps of flow diagram 700 may be performed by a digital processing device, or implemented in analog hardware. It will be noted that the steps of flow diagram 700 may be performed in any suitable order, and certain steps may be omitted entirely.

At step 702, a feature of a Lissajous figure may be identified. Step 702 may be performed in accordance with any of the embodiments described herein, including those described above with reference to step 506 of flow diagram 500 (FIG. 5). For example, a feature of a Lissajous figure may be any of the similarity metrics, shape change metrics and noise metrics described above, any other suitable feature, or any combination of features. It will be understood that "a feature of a Lissajous figure" may refer to one or more features of a Lissajous figure.

At step 704, a feature of a Lissajous figure may be subject to a threshold test. Generally, a threshold test on a value may test any of a number of threshold conditions, including whether the value exceeds a single threshold, whether the value is below a single threshold, or whether the value falls within a specified range or ranges. A threshold test may be fixed, and retrieved by processor 412 (FIG. 4) from ROM 52 or RAM 54 (FIG. 2(*b*)). A threshold test may be dynamic and depend, for example, on past Lissajous figures, on past values of a feature of a Lissajous figure, on one or more additional features of a Lissajous figure, or any combination thereof. In an embodiment, a threshold test may depend on values of the feature applied to multiple time windows within a single Lissajous figure or across multiple Lissajous figures. For example, a single threshold may be the average of the feature applied to a fixed number of past time windows, or may be this average minus a multiple of standard deviations of the feature values. When the feature exceeds this single threshold, the threshold test is passed. The threshold test may also depend on secondary signal quality indicators, such as an electromagnetic noise measuring device or a signal arising from sensor 418 (FIG. 4) indicating a malfunction or undesirable operating condition.

Illustrative embodiments of threshold tests on features of Lissajous figures are presented below. However, it will be understood that any feature of a Lissajous figure may be subject to a threshold test in accordance with step 704, including any of the features described herein. Illustrative embodiments of threshold test failure conditions may include:

1. A similarity metric is less than a threshold.
2. A shape change metric is less than a threshold.
3. A noise metric is greater than a threshold.
4. A rate of a change of a similarity metric is greater than a threshold.
5. A rate of change of a shape change metric is greater than a threshold.

6. A rate of change of a noise metric compared to one or more thresholds. Such a threshold test may be useful, for example, for estimating how operating parameters of the device (e.g., sensor device currents and/or processor filter taps) should be changed to mitigate against the noise now and/or in the future.

If it is determined at step 704 that the feature passes the threshold test, monitoring operations may be performed according to a nominal set of parameters at step 706. This nominal parameter set may correspond to a "normal" operating state of the patient monitoring system. Such a set of parameters may include displaying a measurement calculated from one or more received signals on at least one of display 20 and display 28 (FIG. 2(*a*)), storing a calculated measurement (e.g., in RAM 54 of FIG. 2(*b*)), using a calculated measurement in other calculations performed by the system, or any combination thereof. Such calculations may include a patient condition estimation routine or a patient status prediction routine.

If it is determined at step 704 that the feature does not pass the threshold test, monitoring operations may be performed according to an alternate set of parameters at step 708. This alternate parameter set may correspond to a "low measurement quality" operating state of the patient monitoring system. Such a state may indicate reduced confidence in the ability of the one or more received signals to communicate information about a physiological process. The corresponding parameter set may include displaying a "low quality" warning signal via display 20 or display 28 (FIG. 2(*a*)), or an audible warning via speaker 22 or speaker 30 (FIG. 2(*a*)). The parameter set may also include suppressing the display of a measurement calculated from one or more of the received signals, suppressing the storing of the calculated measurement, suppressing the use of the calculated measurement in other calculations performed by the system, or any combination thereof. In an embodiment, the steps of flow diagram 700 may be carried out by a continuous, non-invasive blood pressure (CNIBP) monitoring system, which may suppress a blood pressure measurement if a feature of a Lissajous figure (e.g., a feature representing a noisy condition, or a feature representing a change in arterial compliance) does not pass a threshold test at step 704.

In an embodiment, steps 704, 706 and 708 need not be performed. Instead, a monitoring system may use a feature of a Lissajous figure (identified at step 702) to adjust monitoring operations that may be based at least in part on one or more received signal. For example, multi-parameter monitor 26 (FIG. 2(*a*)) may provide a measurement estimate of a physiological process on display 28 (FIG. 2(*a*)). This measurement estimate may be calculated by processor 412 (FIG. 4) as a running average of measurements made based at least in part on one or more signals received over a time window. The Lissajous figure feature identified at step 702 may be used to determine the length of this time window. In an embodiment, a feature of a Lissajous figure that indicates lower signal quality may correspond to a wider time window and vice versa. Alternately, the length of the time window may be fixed, but each measurement within the window may be weighted within a running average by the value of an associated feature. In such an embodiment, for example, a low quality measurement may have relatively less influence on the measurement estimate displayed by multi-parameter monitor 26 (FIG. 2(*a*)) than under a "nominal" parameter set. In an embodiment, a low quality measurement may not be included in a measurement estimate (e.g., as determined by a threshold test).

Figure 8:
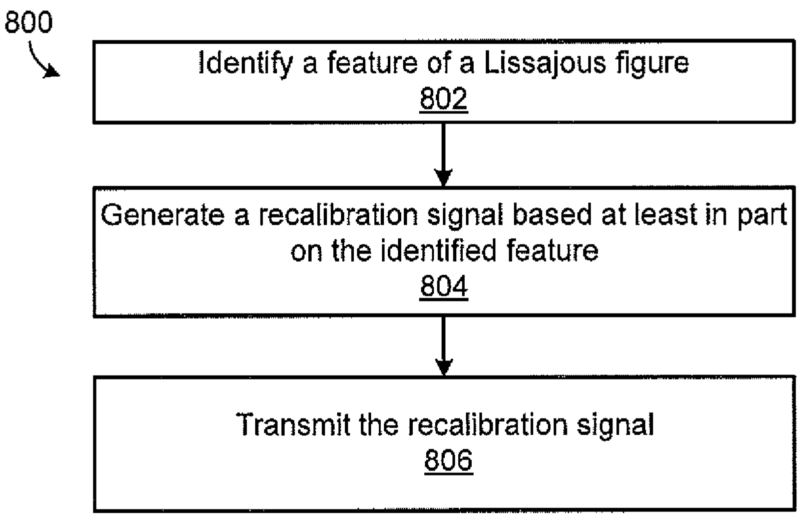
FIG. 8 is a flow diagram of illustrative steps involved in recalibration initiation using a Lissajous figure in accordance with an embodiment.

FIG. 8 is a flow diagram 800 of illustrative steps involved in a recalibration initiation process using a Lissajous figure. The steps of flow diagram 800 may be performed by processor 412 (FIG. 4), or may be performed by any suitable processing device communicatively coupled to monitor 14 (FIGS. 2(*a*) and 2(*b*)). At step 802, a feature of a Lissajous figure may be identified. Step 802 may be performed in accordance with any of the embodiments described herein, including those described above with reference to step 506 of flow diagram 500 (FIG. 5) and step 702 of flow diagram 700 (FIG. 7). For example, a feature of a Lissajous figure may be any of the similarity metrics, shape change metrics and noise metrics described above, or any combination of metrics and/or other suitable features. It will be understood that "a feature of a Lissajous figure" may refer to one or more features of a Lissajous figure.

At step 804, a recalibration signal may be generated based at least in part on the feature identified at step 802. In an embodiment, a recalibration signal may be generated at step 804 based at least in part on a comparison of a Lissajous figure feature and a reference feature value. In an embodiment, a reference feature value is based at least in part on one or more of past values of the recalibration signal, past Lissajous figures, past values of a feature of a Lissajous figure, other features of a Lissajous figure, or any combination thereof. For example, a recalibration signal may be generated based at least in part on whether the feature falls outside a range centered at a reference feature value. The reference feature value may be the average of the feature values calculated for a fixed number of past time windows and the range may include a band of values centered on the average (e.g., a multiple of standard deviations). In an embodiment, the recalibration signal may be further based at least in part on a measurement quality signal (e.g., as described above with reference to flow diagram 500 of FIG. 5). For example, low quality measurements may indicate that a patient is moving or that a sensor has malfunctioned, in which case a recalibration should be delayed until a higher quality measurement can be obtained. Such an embodiment may advantageously reduce time and resources devoted to wasteful recalibrations in periods of low signal quality.

Step 804 may include a threshold test, for example, as described above with reference to step 704 of flow diagram 700 (FIG. 7). Illustrative embodiments of threshold tests on features of Lissajous figures in accordance with step 804 are presented below. However, it will be understood that any feature of a Lissajous figure may be subject to a threshold test in accordance with step 804, including any of the features described herein. Illustrative embodiments of threshold test failure conditions may include:

1. A noise metric is greater than a threshold.
2. A shape change metric is greater than a threshold.
3. A change in a similarity metric since a previous calibration exceeds a threshold.
4. A change in a similarity metric as compared to an archetypal value (e.g., a value derived from an archetypal Lissajous figure based on an idealized shape or a historical data set) exceeds a threshold.

In an embodiment, the steps of flow diagram 800 may be carried out by a continuous, non-invasive blood pressure (CNIBP) monitoring system, and the recalibration signal generated at step 804 may be based at least in part on a feature of a Lissajous figure representing PPG signals from multiple body sites. For example, a feature of a Lissajous figure representing two or more of the received PPG signals may correspond to a change in a patient's blood vessel compliance from a reference value (e.g., a value measured at a previous device calibration). Such a change in compliance may be due to a number of factors, including administration of a drug and patient activity. The identification of a feature of a Lissajous figure corresponding to such a change in compliance may be used to generate a recalibration signal at step 804 that may trigger a recalibration, as described below.

At step 806, a recalibration signal may be transmitted based at least in part on the comparison at step 804. Transmitting a recalibration signal may initiate a recalibration. Initiating a recalibration may include transmitting a recalibration signal to a calibration device 80 (FIG. 4) that includes a command to commence a recalibration process. In an embodiment, initiating a recalibration may include transmitting a recalibration signal to a calibration device 80 (FIG. 4) that schedules a future recalibration process. In an embodiment, initiating a recalibration includes sending a recalibration signal that includes a frequency at which calibration device 80 (FIG. 4) should perform upcoming calibrations. Such an embodiment may be advantageous when a patient is undergoing rapid changes in condition, as reflected in changes in the features of a Lissajous figure representing two or more received signals (such as those received at step 502 of flow diagram 500 of FIG. 5), and more frequent recalibrations are desired than when a patient is in a stable state. In an embodiment, a recalibration may be initiated in response to longer-term changes in Lissajous figure morphology than may indicate a temporary noisy condition (e.g., in a patient monitoring setting, changes that persist for longer than 30 seconds).

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems and apparatuses, but is intended to include variations to and modifications thereof which are within the spirit of the following claims.

What is claimed is:

1. A method for processing physiological monitoring signals, comprising:

monitoring a subject by:

receiving a first electronic signal from a first sensor located at a first body site of a subject; and receiving a second electronic signal from a second sensor located at a second body site of a subject, wherein the second body site is different from the first body site;

using processor equipment for:

calculating a Lissajous figure based at least in part on the first and second electronic signals;

identifying at least one feature of the Lissajous figure; and determining information regarding the monitoring of the subject based at least in part on the at least one feature; and outputting at least a portion of the information to an output device.

2. The method of claim 1, wherein the first and second electronic signals are photoplethysmograph signals.

3. The method of claim 1, wherein calculating a Lissajous figure comprises calculating at least one time derivative of at least one of the first and second electronic signals.

4. The method of claim 1, wherein calculating a Lissajous figure comprises time-shifting at least one of the first and second electronic signals.

5. The method of claim 1, further comprising using processor equipment for:

transforming the first electronic signal into a first transformed signal based at least in part on a continuous wavelet transformation, generating a first scalogram from the transformed signal, and identifying, within the first scalogram, a first selected signal associated with a selected scale, wherein calculating a Lissajous figure is based at least in part on the first selected signal.

6. The method of claim 1, wherein the at least one feature comprises a first principal component.

7. The method of claim 1, wherein the at least one feature comprises a shape change metric which is based on at least one difference between different cycles in the Lissajous figure.

8. The method of claim 1, further comprising using processor equipment for calculating a physiological measurement based at least in part on the at least one feature.

9. The method of claim 1, further comprising initiating a recalibration based at least in part on the at least one feature.

10. The method of claim 1, wherein identifying at least one feature comprises:

recording a plurality of Lissajous figures associated with a plurality of points in time;

calculating an archetypal Lissajous figure based at least in part on the recorded plurality of Lissajous figures; and comparing the Lissajous figure to the archetypal Lissajous figure.

11. The method of claim 1, wherein the at least one feature comprises an area enclosed by one or more trajectories of the Lissajous figure.

12. The method of claim 1, wherein the at least one feature comprises an area metric based on an area in between different cycles of the Lissajous figure.

13. A system for processing physiological monitoring signals, comprising:

a signal input, capable of receiving a first electronic signal from a first sensor located at a first body site of a subject, and capable of receiving a second electronic signal from a second sensor located at a second body site of the subject, wherein the second body site is different from the first body site;

a signal output, capable of outputting an electronic signal representative of information regarding the monitoring of the subject; and a processor, communicably coupled to the signal input and the signal output, the processor being capable of:

monitoring the subject based at least in part on the first and second electronic signals;

calculating a Lissajous figure based at least in part on the first and second electronic signals;

identifying at least one feature of the Lissajous figure;

determining information regarding the monitoring of the subject based at least in part on the at least one feature; and outputting at least a portion of the information to the output device.

14. The system of claim 13, wherein the first and second electronic signals are photoplethysmograph signals.

15. The system of claim 13, wherein calculating a Lissajous figure comprises calculating at least one time derivative of at least one of the first and second electronic signals.

16. The system of claim 13, wherein the processor is further capable of:

transforming the first electronic signal into a first transformed signal based at least in part on a continuous wavelet transformation, generating a first scalogram from the transformed signal, and identifying, within the first scalogram, a first selected signal associated with a selected scale, wherein calculating a Lissajous figure is based at least in part on the first selected signal.

17. The system of claim 13, wherein the at least one feature comprises a first principal component.

18. The system of claim 13, wherein the at least one feature comprises a shape change metric which is based on at least one difference between different cycles in the Lissajous figure.

19. The system of claim 13, wherein the processor is further capable of calculating a physiological measurement based at least in part on the at least one feature.

20. The system of claim 13, wherein the processor is further capable of initiating a recalibration based at least in part on the at least one feature.

21. The system of claim 13, wherein identifying at least one feature comprises:

recording a plurality of Lissajous figures associated with a plurality of points in time;

calculating an archetypal Lissajous figure based at least in part on the recorded plurality of Lissajous figures;

comparing the Lissajous figure to the archetypal Lissajous figure.

22. Non-transitory computer-readable medium for use in processing physiological monitoring signals, the non-transitory computer-readable medium having computer program instructions recorded thereon for:

monitoring a subject by:

receiving a first electronic signal from a first sensor located at a first body site of a subject; and receiving a second electronic signal from a second sensor located at a second body site of a subject, wherein the second body site is different from the first body site;

calculating a Lissajous figure based at least in part on the first and second electronic signals;

identifying at least one feature of the Lissajous figure; and determining information regarding the monitoring of the subject based at least in part on the at least one feature.

* * * * *